United States Patent
Meagher et al.

(10) Patent No.: US 11,366,116 B1
(45) Date of Patent: Jun. 21, 2022

(54) REAL TIME AUTONOMOUS SURVEILLANCE OF PATHOGENS

(71) Applicant: National Technology & Engineering Solutions of Sandia, LLC, Albuquerque, NM (US)

(72) Inventors: Robert Meagher, Mountain House, CA (US); Ronald F. Renzi, Rexford, NY (US); Cameron Scott Ball, Los Altos, CA (US); Aashish Priye, Livermore, CA (US); Jonathan Ivers Helm, Oakland, CA (US); Bryan Carson, Tijeras, NM (US); Stanley Alan Langevin, Seattle, WA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 191 days.

(21) Appl. No.: 15/951,920

(22) Filed: Apr. 12, 2018

Related U.S. Application Data

(60) Provisional application No. 62/484,689, filed on Apr. 12, 2017.

(51) Int. Cl.
| | | |
|---|---|---|
| *G01N 33/569* | (2006.01) | |
| *G01N 33/548* | (2006.01) | |
| *G01N 33/53* | (2006.01) | |

(52) U.S. Cl.
CPC ... *G01N 33/56983* (2013.01); *G01N 33/5304* (2013.01); *G01N 33/548* (2013.01); *G01N 2469/10* (2013.01)

(58) Field of Classification Search
CPC .................................. G01N 22/56983
USPC .......................................... 435/287.2
See application file for complete search history.

(56) References Cited

U.S. PATENT DOCUMENTS

| | | | | |
|---|---|---|---|---|
| 5,089,385 | A | * | 2/1992 | Kiel ................. C12M 29/10 435/173.1 |
| 5,320,808 | A | * | 6/1994 | Holen ................. B01L 3/508 422/64 |
| 5,583,478 | A | | 12/1996 | Renzi |
| 5,777,734 | A | | 7/1998 | Flower et al. |
| 6,084,205 | A | | 7/2000 | Sheaffer et al. |
| 6,410,278 | B1 | | 6/2002 | Notomi et al. |
| 6,832,787 | B1 | | 12/2004 | Renzi |
| 6,918,573 | B1 | | 7/2005 | Renzi |
| 6,926,313 | B1 | | 8/2005 | Renzi |
| 6,966,336 | B1 | | 11/2005 | Renzi |
| 6,998,598 | B2 | | 2/2006 | Horn et al. |

(Continued)

FOREIGN PATENT DOCUMENTS

WO   WO 2015/013004 A1   1/2015

OTHER PUBLICATIONS

Meagher et al., Report No. SAND2016-3847PE, Apr. 1, 2016, Sandia National Lab (Year: 2016).*

(Continued)

*Primary Examiner* — Holly Kipouros
(74) *Attorney, Agent, or Firm* — Medley, Behrens & Lewis, LLC; Helen S. Baca; Madelynne J. Farber

(57) ABSTRACT

The present invention relates, in part, to systems configured to obtain samples from an organism in an autonomous manner. Such systems can employ a cartridge configured to provide bait to attract an organism, as well as channels to store and/or test samples obtained from the organism.

19 Claims, 9 Drawing Sheets

(56) References Cited

U.S. PATENT DOCUMENTS

| | | |
|---|---|---|
| 7,182,371 B1 | 2/2007 | Renzi |
| 7,311,882 B1 | 12/2007 | Renzi |
| 7,351,380 B2 | 4/2008 | Simmons et al. |
| 7,452,507 B2 | 11/2008 | Renzi et al. |
| 7,553,455 B1 | 6/2009 | Renzi et al. |
| 7,592,139 B2 | 9/2009 | West et al. |
| 8,047,829 B1 | 11/2011 | Sommer et al. |
| 8,162,149 B1 | 4/2012 | Perroud et al. |
| 8,163,254 B1 | 4/2012 | Renzi et al. |
| 8,394,312 B1 | 3/2013 | Sommer et al. |
| 8,398,839 B1 | 3/2013 | Morales et al. |
| 8,426,135 B1 | 4/2013 | West et al. |
| 8,518,346 B1 | 8/2013 | Chirica et al. |
| 8,585,916 B2 | 11/2013 | Perroud et al. |
| 8,585,986 B1 | 11/2013 | Renzi |
| 8,808,588 B1 | 8/2014 | Simmons et al. |
| 8,828,736 B2 | 9/2014 | Perroud et al. |
| 8,900,807 B2 | 12/2014 | Owen et al. |
| 8,912,502 B2 | 12/2014 | Derzon et al. |
| 8,940,147 B1 | 1/2015 | Bartsch et al. |
| 9,074,243 B2 | 7/2015 | Tanner et al. |
| 9,074,249 B2 | 7/2015 | Tanner et al. |
| 9,170,340 B1 | 10/2015 | Derzon et al. |
| 9,322,014 B1 | 4/2016 | VanderNoot et al. |
| 9,404,913 B2 | 8/2016 | Perroud et al. |
| 9,579,649 B2 | 2/2017 | Renzi et al. |
| 9,857,370 B2 | 1/2018 | Harper et al. |
| 2010/0105029 A1* | 4/2010 | Ririe .......... B01L 7/52 435/6.12 |
| 2010/0297640 A1* | 11/2010 | Kumar .......... B01L 7/52 435/6.11 |
| 2013/0171643 A1 | 7/2013 | Kubota et al. |
| 2014/0134078 A1* | 5/2014 | Njoroge .......... C12N 15/101 422/527 |
| 2016/0129445 A1* | 5/2016 | Corey .......... C12Q 1/6806 435/286.1 |

OTHER PUBLICATIONS

Roy et al., Magnetic microsphere-based mixers for microdroplets, 2009, Physics of Fluids, 21 (Year: 2009).*

U.S. Appl. No. 15/008,285, filed Jan. 27, 2016, Meagher et al.

U.S. Appl. No. 15/447,581, filed Mar. 2, 2017, Ball et al.

Aonuma H et al., "Rapid identification of *Plasmodium*-carrying mosquitoes using loop-mediated isothermal amplification," *Biochem. Biophys. Res. Commun.* 2008;376(4):671-6.

Ball C et al., "A simple micro check valve for microfluidic point-of-care diagnostics," *Sandia Report No. SAND2016-1087C*, proposed for presentation at the Society for Laboratory Automation and Screening (SLAS) conference held Jan. 24-27, 2016 in San Diego, CA (1 p.).

Ball CS et al., "A simple check valve for microfluidic point of care diagnostics," *Lab Chip* 2016;16(22):4436-44.

Ball CS et al., "Quenching of unincorporated amplification signal reporters in reverse-transcription loop-mediated isothermal amplification enabling bright, single-step, closed-tube, and multiplexed detection of RNA viruses," *Anal. Chem.* 2016;88:3562-8.

Ball CS et al., "Real-time autonomous surveillance for vector-borne pathogens," *Sandia Report No. SAND2016-10154C*, proposed for presentation at the MicroTAS 2016 conference held on Oct. 9-13, 2016 in Dublin, Ireland (1 p.).

Ball CS et al., "Real-time autonomous surveillance for vectorborne pathogens," *Sandia Report No. SAND2016-9878C*, abstract for MicroTAS 2016 conference held on Oct. 9-13, 2016 in Dublin, Ireland (2 pp.).

Barker CM et al., "Seasonal abundance of *Culex tarsalis* and *Culex pipiens* complex mosquitoes (Diptera: Culicidae) in California," *J. Med. Entomol.* 2010;47(5):759-68.

Barker CM, "Spatial and temporal patterns in mosquito abundance and virus transmission in California," Ph.D. dissertation in Entomology in the Office of Graduate Studies of the University of California Davis, 2008, front page, abstract, and chapter 1, pp. i-vi and 1-16 (24 pp.).

Bashar K et al., "Seasonal abundance of *Anopheles* mosquitoes and their association with meteorological factors and malaria incidence in Bangladesh," *Parasit. Vectors* 2014;7:442 (10 pp.).

Beier JC et al., "Attractive toxic sugar bait (ATSB) methods decimate populations of Anopheles malaria vectors in arid environments regardless of the local availability of favoured sugar-source blossoms," *Malar. J.* 2012;11:31 (7 pp.).

Chen Y et al., "Flying insect detection and classification with inexpensive sensors," *J. Vis. Exp.* 2014;(92):e52111 (9 pp.).

Drakeley C et al., "The epidemiology of *Plasmodium falciparum* gametocytes: weapons of mass dispersion," *Trends Parasitol.* 2006;22(9):424-30.

Eiras AE et al., "Development of the gravid Aedes trap for the capture of adult female container-exploiting mosquitoes (Diptera: Culicidae)," *J. Med. Entomol.* 2014;51(1):200-9.

Fikrig K et al., "Assessment of synthetic floral-based attractants and sugar baits to capture male and female *Aedes aegypti* (Diptera: Culicidae)," *Parasit. Vectors* 2017;10(1):32 (9 pp.).

Golenda CF et al., "*Plasmodium falciparum* and *P. berghei*: detection of sporozoites and the circumsporozoite proteins in the saliva of *Anopheles stephensi* mosquitoes," *Parasitol. Res.* 1992;78(7):563-9.

Iwamoto T et al., "Loop-mediated isothermal amplification for direct detection of *Mycobacterium tuberculosis* complex, *M. avium*, and *M. intracellulare* in sputum samples," *J. Clin. Microbiol.* 2003;41(6):2616-22.

Lau YL et al., "Colorimetric detection of dengue by single tube reverse-transcription-loop-mediated isothermal amplification," *PLoS One* 2015;10(9):e013869 (9 pp.).

Lothrop HD et al., "Use of scented sugar bait stations to track mosquito-borne arbovirus transmission in California," *J. Med. Entomol.* 2012;49(6):1466-72.

Meagher R et al., "An integrated microfluidic system enabling real-time autonomous field surveillance for vector-borne pathogens," *Sandia Report No. SAND2016-11989C*, proposed for presentation at the American Institute of Chemical Engineers annual conference held on Nov. 13-18, 2016 in San Francisco, CA (15 pp.).

Meagher R et al., "An integrated microfluidic system enabling real-time autonomous field surveillance for vector-borne pathogens," abstract No. 462494 for the American Institute of Chemical Engineers annual conference held on Nov. 13-18, 2016 in San Francisco, CA (1 p.).

Meagher R et al., "Real-time autonomous biosurveillance for vector-borne viral pathogens (SMART Traps)," *Sandia Report No. SAND2016-1854PE*, proposed for presentation at the DTRA Biosurveillance Ecosystem Technical Interchange Meeting held on Feb. 9-10, 2016 in Falls Church, VA (12 pp.).

Meagher R et al., "Real-time, autonomous biosurveillance for vector-borne viral pathogens," *Sandia Report No. SAND2015-1369PE*, proposed for presentation at the DTRA Biosurveillance Ecosystem Technical Interchange Meeting held on Feb. 24-25, 2015 in Falls Church, VA (34 pp.).

Meagher R et al., "Real-time, autonomous biosurveillance for vector-borne viral pathogens (SMART Traps)," *Sandia Report No. SAND2016-5984C*, proposed for presentation at the Arizona Department of Health Services' conference on Analytic Solutions for Real-Time Biosurveillance: Assessing Risk for Emerging Arboviral Disease held on Jun. 14-15, 2016 in Phoenix, AZ (27 pp.).

Meagher RJ et al., "Rapid, closed-tube multiplexed detection of viral and bacterial pathogens by isothermal amplification with streamlined sample prep," *Sandia Report No. SAND2016-1855C*, proposed for presentation at the American Society for Microbiology General Meeting held on May 31, 2015-Jun. 2, 2015 in New Orleans, LA (1 p.).

Meagher RJ et al., "Real-time autonomous biosurveillance for vectorborne pathogens (Smart Traps)," *Sandia Report No. SAND2016-1853D*, proposed for presentation at the DTRA Biosurveillance Ecosystem Technical Interchange Meeting held on Feb. 8-10, 2016 in Falls Church, VA (1 p.).

(56) References Cited

OTHER PUBLICATIONS

Meagher RJ et al., "Smart phone-enabled diagnostic platform for detection of pathogen nucleic acids," *Sandia Report No. SAND2016-9879C*, abstract for MicroTAS 2016 conference held on Oct. 9-13, 2016 in Dublin, Ireland (2 pp.).

Meagher RJ et al., "Smart phone-enabled diagnostic platform for detection of pathogen nucleic acids," *Sandia Report No. SAND2016-3848A*, abstract for MicroTAS 2016 conference held Oct. 9-13, 2016 in Dublin, Ireland (2 pp.).

Meagher RJ et al., "Smart phone-enabled diagnostic platform for detection of pathogen nucleic acids," *Sandia Report No. SAND2016-2192C*, proposed for presentation at the Molecular Medicine Tri conference held on Mar. 7-9, 2016 in San Francisco, CA (1 p.).

Meagher RJ, "Real-time, autonomous biosurveillance for vector-borne viral pathogens," *Sandia Report No. SAND2015-3556C*, proposed for presentation at the DTRA CBD Science & Technology Conference held on May 11-14, 2015 in St Louis, MO (17 pp.).

Mohon AN et al., "A new visually improved and sensitive loop mediated isothermal amplification (LAMP) for diagnosis of symptomatic falciparum malaria," *Acta Trop.* 2014;134:52-7.

Moore A et al., "Automated identification of flying insects by analysis of wingbeat frequencies," *J. Econ. Entomol.* 1986;79(6):1703-6.

Mori Y et al., "Detection of loop-mediated isothermal amplification reaction by turbidity derived from magnesium pyrophosphate formation," *Biochem. Biophys. Res. Commun.* 2001;23;289(1):150-4.

Msugh-Tier MM et al., "Sporozoite infection rates of female Anopheline mosquitos in Makurdi, an endemic area for malaria in Central Nigeria," *Int'l J. Entomol. Res.* 2014;2(2):103-15.

Mullen ER et al., "Laser system for identification, tracking, and control of flying insects," *Opt. Express* 2016;24(11):11828-38.

Notomi T et al., "Loop-mediated isothermal amplification (LAMP): principle, features, and future prospects," *J. Microbiol.* 2015;53(1):1-5.

Notomi T et al., "Loop-mediated isothermal amplification of DNA," *Nucleic Acids Res.* 2000;28(12):e63 (7 pp.).

Nyasembe VO et al., "*Plasmodium falciparum* infection increases *Anopheles gambiae* attraction to nectar sources and sugar uptake," *Curr. Biol.* 2014;24(2):217-21.

Oduola AO et al., "Malaria transmission risk indices of three *Anopheles* species in selected rural communities in Oyo state South-Western Nigeria," *Int'l J. Tropical Med.* 2012;7(1):42-8.

Parida M et al., "Real-time reverse transcription loop-mediated isothermal amplification for rapid detection of West Nile virus," *J. Clin. Microbiol.* 2004;42(1):257-63.

Priye A et al., "A smartphone actuated isothermal amplification platform for rapid detection of nucleic acid assays," *Sandia Report No. SAND2016-0718C*, proposed for presentation at the Society of Laboratory Automation conference held on Jan. 24-27, 2016 in San Diego, CA (1 p.).

Priye A et al., "A smartphone-based diagnostic platform for rapid detection of Zika, chikungunya, and dengue viruses," *Sci. Rep.* 2017;7:44778 (10 pp.).

Priye A et al., "An automated smart-phone based detection platform enables real-time isothermal amplification (RT-LAMP) for mobile healthcare," *Sandia Report No. SAND2015-8514C*, proposed for presentation at the Lab On Chip World Congress held on Sep. 28-30, 2015 in San Diego, CA (1 p.).

Priye A et al., "Loop-mediated isothermal amplification (LAMP): an insight into reaction mechanism and application in point-of-care diagnostics," *Sandia Report No. SAND2016-11965C*, proposed for presentation at the American Institute of Chemical Engineers conference held on Nov. 13-18, 2016 in San Francisco, CA (1 p.).

Reisen WK et al., "Bionomics of *Culex tarsalis* (Diptera: Culicidae) in relation to arbovirus transmission in southeastern California," *J. Med. Entomol.* 1995;32(3):316-27.

Rudolph DL et al., "Detection of acute HIV-1 infection by RT-LAMP," *PLoS One* 201520;10(5):e0126609 (13 pp.).

Tanner NA et al., "Simultaneous multiple target detection in real-time loop-mediated isothermal amplification," *Biotechniques* 2012;53(2):81-9.

Wang R et al., "Micro-Doppler measurement of insect wing-beat frequencies with W-band coherent radar," *Sci. Rep.* 2017;7(1):1396 (8 pp.).

Wheeler SS et al., "Surveillance for Western Equine Encephalitis, St. Louis Encephalitis, and West Nile Viruses using reverse transcription loop-mediated isothermal amplification," *PLoS One* 2016;11(1):e0147962 (17 pp.).

\* cited by examiner

REAL TIME AUTONOMOUS SURVEILLANCE OF PATHOGENS

CROSS-REFERENCE TO RELATED APPLICATION

This application claims the benefit of U.S. Provisional Application No. 62/484,689, filed Apr. 12, 2017, which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates, in part, to systems configured to obtain samples from an organism in an autonomous manner. Such systems can employ a cartridge configured to provide bait to attract an organism, as well as channels to store and/or test samples obtained from the organism.

BACKGROUND OF THE INVENTION

Real time surveillance of pathogens remains a technological challenge. For instance, proposals include field-based testing of organisms that can potentially harbor threatening pathogens, but such field testing can be labor intensive. Exemplary field tests can include use of sugar baits to attract arthropod vectors (e.g., mosquitos or ticks), in which samples are collected and then tested at an off-site laboratory. Additional systems are desired which minimize human contact and exposure to pathogens, while simplifying sample collection and testing.

SUMMARY OF THE INVENTION

We have developed a system that detects the presence of pathogens including viruses, parasites, or bacteria in arthropod vectors, primarily (but not limited to) mosquitoes. The device, known as the Smart Trap, relies upon passive collection of saliva from mosquitoes on a sugar bait, and then performs an assay to detect the presence of pathogen nucleic acid (e.g., DNA or RNA) deposited on the sugar bait. The system runs autonomously and can be deployed in remote locations, with wireless transmission of results of pathogen incidence, on a daily basis.

In a first aspect, the present invention features a system including: a port configured to receive an organism; a cartridge (e.g., configured to obtain a test sample from the organism within the port and to conduct an assay for detecting a target nucleic acid indicating presence of a pathogenic nucleic acid in the test sample, where at least one chamber is configured to store one or more agents for conducting the assay and where a portion of the cartridge is accessible to the organism within the port); a heating module configured to heat a portion of the cartridge; a detection module configured to detect a signal from the cartridge; a motor module configured to move the cartridge in proximity to the port, the heating module, and the detection module; and a processing module configured to generate a signal to the heating module, the detection module, and/or the motor module and configured to receive a detectable signal from the detection module.

In some embodiments, the cartridge includes one or more unidirectional check valves. In one embodiment, the cartridge includes a feeding well configured to obtain the test sample from the organism; one or more assay channels including the one or more agents to conduct the assay; and one or more unidirectional check valves configured to deliver the test sample to the one or more assay channels.

In other embodiments, the cartridge includes: a feeding well configured to obtain the test sample from the organism; and one or more assay channels including the one or more agents to conduct the assay. In yet other embodiments, the cartridge includes: a fluid reservoir including a fluid (e.g., a buffer) and a membrane disposed in proximity to the fluid reservoir and configured to dispense the buffer upon actuation.

In some embodiments, the cartridge includes: a feeding well including a dehydrated bait or a solid bait; a fluid reservoir including a buffer and a membrane configured to dispense the buffer upon actuation; a first unidirectional check valves configured to deliver the buffer to the feeding well; one or more assay channels including the one or more agents to conduct the assay; a second unidirectional check valves configured to deliver the test sample from the feeding well to the one or more assay channels; and/or an optional toothed track along an edge of the cartridge to engage the motor module. In other embodiments, the cartridge is a disposable cartridge configured for use in a rotary carousel. In some embodiments, the cartridge is configured to be disposed within a recessed portion of a carousel, where the carousel is configured to include a plurality of recessed portion and each recessed portion is configured to house a cartridge. In yet other embodiments, the system further includes a motor module configured to rotate the carousel and move at least one cartridge in proximity to the port, the heating module, and the detection module.

In some embodiments, the system further includes: an actuator (e.g., configured to actuate a membrane of the cartridge, to dispense a fluid into one or more assay chambers, and/or to apply pressure within a channel of the cartridge).

In some embodiments, the feeding well further includes a ball bearing (e.g. a metal ball bearing). In further embodiments, the system includes a spinning magnet configured to rotate the ball bearing within the feeding well.

In some embodiments, the system further includes: a network relay module configured to relay an electronic signal from the processing module. In some embodiments, the network relay module can include a coordinator link configured to communicate the electronic signal from a first system to a second system, a first transmission link configured to relay the electronic signal from the system to an internet-accessible device, and/or a second transmission link configured to relay the electronic signal from the system to a cloud-based data storage system or from the internet-accessible device to the cloud-based data storage system. In some embodiments, the network relay further includes one or more microprocessor to analyze, parse, or score the electronic signal.

In a second aspect, the present invention features an assembly including: a system (e.g., any described herein); a field trap configured to house the system and to trap a plurality of organisms; a network relay module configured to relay an electronic signal from the processing module; and an external power source module configured to provide power to the system, the field trap, and/or the network relay module. In some embodiments, the field trap can include an entry port configured to receive a plurality of organisms.

In a third aspect, the present invention features a system including: a port configured to receive an organism; a plurality of cartridges (e.g., a plurality of any cartridge described herein, in which each cartridge can be the same or different); a holder configured to store the plurality of cartridges; a heating module configured to heat a portion of at least one cartridge; a detection module configured to detect a signal from at least one cartridge; a motor module configured to move at least one cartridge in proximity to the port, the stack holder, the heating module, and the detection module; and a processing module configured to generate a signal to the heating module, the detection module, and/or the motor module and configured to receive a detectable signal from the detection module.

In some embodiments, at least one cartridge is configured to obtain a test sample from the organism within the port and to conduct an assay for detecting a target nucleic acid indicating presence of a pathogenic nucleic acid in the test sample, where at least one chamber is configured to store one or more agents for conducting the assay and where a portion of the cartridge is accessible to the organism within the port.

In a fourth aspect, the present invention features a system including: a port configured to receive an organism; a cartridge configured to obtain a test sample from the organism within the port; an actuator configured to actuate the membrane of the cartridge; a heating module configured to heat a portion of the cartridge; a detection module configured to detect a signal from the cartridge; a motor module configured to engage the toothed track of the cartridge and to move the cartridge in proximity to the port, the heating module, and the detection module; a processing module configured to generate a signal to the heating module, the detection module, and/or the motor module and configured to receive a detectable signal from the detection module; and a network relay module configured to relay an electronic signal from the processing module.

In some embodiments, the cartridge includes: a feeding well including a bait, where the feeding well is configured to be accessible to the organism within the port; a fluid reservoir including a buffer and a membrane configured to dispense the buffer upon actuation; a first unidirectional check valves configured to deliver the buffer to the feeding well; one or more assay channels including one or more agents to conduct an assay; a second unidirectional check valves configured to deliver the test sample from the feeding well to the one or more assay channels; and a toothed track along an edge of the cartridge.

In any embodiment herein, the agents in the one or more assay channels are on-chip, dried reagents.

In any embodiment herein, the one or more agents include a first primer, a first quench probe, a first signal probe, a second primer, a second quench probe, and/or a second signal probe.

In any embodiment herein, the assay includes: a first primer including a first nucleic acid sequence having sufficient complementarity to a site in the pathogenic nucleic acid; and a quench probe including a second nucleic acid sequence having sufficient complementarity to a first portion of the first primer and further including a quencher label operably linked to the second nucleic acid sequence, where a melting temperature $T_m$ of the quench probe is less than about 65° C.

In any embodiment herein, the one or more agents include a stabilizing agent. In any embodiment herein, the pathogenic nucleic acid is obtained from Zika virus, Zaire ebolavirus (EBOV), West Nile Virus (WNV), Chikungunya Virus (CHIKV), Western Equine Encephalitis Virus (WEEV), St. Louis Encephalitis Virus (SLEV), Dengue Virus (DENV), Marburg virus (MARV), Sudan ebolavirus (SUDV), Bundibugyo virus (BDBV), Yellow Fever Virus (YFV), Japanese Encephalitis Virus (JEV), Hepatitis C virus (HCV), Eastern Equine Encephalitis Virus (EEEV) Venezuelan Equine Encephalitis Virus (VEEV), Sindbis virus (SINV), Ross River virus (RRV), influenza virus, hantavirus, Rift Valley Fever virus, Crimean-Congo hemorrhagic fever virus, Lassa Fever virus, or norovirus, or any other described herein.

In any embodiment herein, the organism is a mosquito.

In any embodiment herein, the cartridge is configured to conduct a multiplexed assay.

In any embodiment herein, the system includes: a network relay module configured to relay an electronic signal from the processing module; a fluid dispensing module configured to deliver a fluid (e.g., a buffer and/or a liquid bait) to the cartridge; a processing module including a portable device (e.g., a smart phone); and/or a detection module including a portable device (e.g., a smart phone).

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

A "target sequence" as used herein is a polynucleotide (e.g., as defined herein, including a DNA, RNA, or DNA/RNA hybrid, as well as modified forms thereof) that includes a "target site." The terms "target site" or "target protospacer DNA" are used interchangeably herein to refer to a nucleic acid sequence present in a target genomic sequence (e.g., DNA or RNA in a host or pathogen) to which a targeting portion of the guiding component will bind provided sufficient conditions (e.g., sufficient complementarity) for binding exist. Suitable DNA/RNA binding conditions include physiological conditions normally present in a cell. Other suitable DNA/RNA binding conditions (e.g., conditions in a cell-free system) are known in the art; see, e.g., Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001).

Other features and advantages of the invention will be apparent from the following description and the claims.

DETAILED DESCRIPTION OF THE INVENTION

Figure 1:
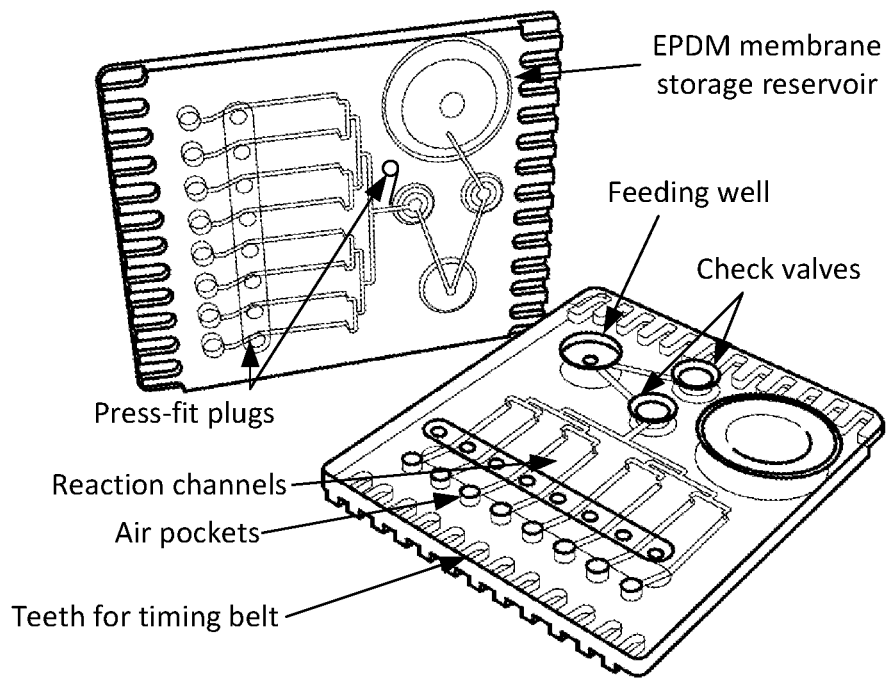
FIG. 1 provides assembled microfluidic chips (exemplary cartridges) filled with rehydrated food coloring for reaction channel visualization.

The present invention relates to systems for conducting autonomous surveillance of a pathogen. The system (e.g., a Smart Trap) includes a cartridge (e.g., configured to detect a target nucleic acid, including a plurality of cartridges provided on a carousel or in a stack), a port configured to receive an organism and obtain a test sample from the organism (e.g., an organism carrying a target nucleic acid, which in turn can indicate the presence of a pathogen infecting that organism), a heating module, a detection module, and a processing module. The system can include a motor module (e.g., a stepper motor configured to move the cartridge, to exchange a first cartridge with a second cartridge, and/or to actuate a belt drive module to deliver a plurality of cartridges in an autonomous manner; or a rotary motor configured to rotate the cartridge within a carousel and/or to move the cartridge from one module to another module). In particular embodiments, the cartridge is configured to conduct an assay that employs Reverse-Transcription Loop Mediated Isothermal Amplification (RT-LAMP) to provide endpoint detection in a sensitive and rapid manner. Additional details follow.

Cartridges

The present system can include any useful cartridge (e.g., such as a closed-tube cartridge). The cartridge can include one or more chambers, which can be configured to substantially enclose a fluid or a substance in the fluidic cartridge. Such chamber can include one or more inlets, outlets, fluidic opening (e.g., vias), fluidic barriers, or any other structure to allow for fluidic communication between one or more chambers, sample ports, vents, etc. Exemplary chambers include a channel, a reservoir, etc., having any useful geometry or dimension. In some instances, the valve housing itself can serve as a chamber.

The cartridge can be configured to conduct any useful assay, such as a Reverse-Transcription Loop Mediated Isothermal Amplification (RT-LAMP) reaction or QUASR (see, e.g., Ball C S et al., "Quenching of unincorporated amplification signal reporters in reverse-transcription loop-mediated isothermal amplification enabling bright, single-step, closed-tube, and multiplexed detection of RNA viruses." *Anal. Chem.* 2016; 88:3562-8). Other nucleic acid amplification reactions can be conducted (e.g., polymerase chain reaction (PCR), quantitative reverse-transcription polymerase chain reaction (qRT-PCR)).

The chambers can be designated for a particular use. Particular uses for such chambers include a sample chamber for receiving and/or storing a test sample, an incubation chamber for incubating a test sample (e.g., to amplify one or more targets), a reagent chamber containing one or more reagents for detecting one or more targets (e.g., on-chip, dried reagents), a sterilization chamber containing one or more reagents to sterilize or disinfect the test sample (e.g., containing one or more sterilization agents, as described herein), an assay chamber for conducting one or more assays to detect one or more targets, and/or a waste chamber for storing one or more by-products of the assay. Each of these chambers can be interconnected by a valve (e.g., a check valve, such as any described herein) and/or a channel that can optionally include such a valve in its fluidic path.

Each chamber can be functionalized in any manner, such as by coating (e.g., with a polymer, a gel, etc.), treating (e.g., with a silane, an amide, plasma, UV, ozone, etc. to change the surface chemistry of a surface, such as by modifying hydrophilicity and/or biocompatibility), passivating (e.g., with wax), purging (e.g., with an inert gas and/or under vacuum), and/or sterilizing with a sterilization agent (e.g., bleach, UV, ozone, etc.).

Materials for Cartridges

The present cartridges can be formed from any useful material. Exemplary materials include a polymer, such as polymethyl methacrylate (PMMA), polyester, polyethylene terephthalate (PET, e.g., biaxially-oriented PET or bo-PET, such as Mylar®), an acrylic polymer, poly(dimethylsiloxane) (PDMS), polycarbonate (PC), cyclo-olefin copolymer (COC), cyclo-olefin polymer (COP), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof; a thermoplastic material; an elastomeric material; silicon; glass; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organo-tin compounds), antioxidants (e.g., phenols or amines), and/or UV stabilizers (e.g., benzophenones or salicylates). Such materials can be provided in any useful form, such as in one or more layers that can be laminated to provide the assembled cartridge.

Exemplary thermoplastic materials (e.g., for a prestressed spring) include PMMA, PET, PC, polycyclic olefin (PCO), acrylonitrile butadiene styrene (ABS), polylactic acid (PL), PE, PTFE, etc. In particular non-limiting embodiments, a thermoplastic material is one capable of being cut, patterned, molded, or bent by applying a heat source (e.g., a laser). Exemplary elastomeric materials (e.g., for an elastomeric pad) include silicone, rubber, fluorosilicone, nitrile rubber, PDMS, etc.

The apparatus (e.g., cartridge) can include one or more layers containing one or more adhesive materials. Exemplary adhesive materials include an acrylate (e.g., a silicone acrylate, a polymethyl acrylate, a polymethyl methacrylate, including those formed from 2-ethyl hexyl acrylate or n-butyl acrylate monomers, etc.), a polyolefin (e.g., polyethylene, polybutene, or polypropylene), an acetate (e.g., an ethylene-vinyl acetate), a styrene (e.g., a polystyrene, a styrene block copolymer (e.g., styrene-butadiene-styrene, styrene-isoprene-styrene, styrene-ethylene/butylene-styrene, or styrene-ethylene/propylene), an isobutylene (e.g., polyisobutylene, a copolymer of isobutylene with isoprene, including copolymers thereof), a rubber (e.g., a polyisoprene, a silicone rubber, a polychloroprene, a polyisobutylene, as well as copolymers of any of these), a polyamide, a polyester, a polyurethane, a polynitrile (e.g., nitrile butadiene rubber), a polyether (e.g., a vinyl ether), etc. The adhesive material can be provided in any useful format. For instance, the adhesive material can be provided as a substantially planar substrate having one or more removed portions to define one or more chambers. Such layers can be provided as a backing layer (e.g., a polyester layer) coated with an adhesive material (e.g., an acrylic). In some embodiments, the adhesive material is sterilized (e.g., by steam, ethylene oxide, ozone, bleach, radiation, etc.).

Systems

An exemplary system can include one or more modules or components to facilitate performing assays with the cartridge (e.g., microfluidic cartridge). In one non-limiting instance, the system includes a cartridge (e.g., configured to provide a signal indicative of the presence or absence of a target analyte, such as a target nucleic acid, by way of conducting an assay reaction), a heating module (e.g., a heater configured to conduct one or more assay reactions, including RT-LAMP or QUASR-based methods), a detection module (e.g., configured to obtain a signal from the cartridge), and a processing module (e.g., a processing device configured to analyze a detectable signal).

The system can include a motor module (e.g., a stepper motor configured to move the cartridge, to exchange a first cartridge with a second cartridge, and/or to actuate a belt drive module to deliver a plurality of cartridges in an autonomous manner). The motor module can include any useful motor, e.g., a brushed DC motor, a stepper motor, a solenoid, a servo motor, a linear actuator, as well as combinations thereof.

Optionally, the system can include a power source and/or a network relay module (e.g., configured to relay an electronic signal from the processing module, which can be indicative of a result from the detectable signal obtained from the detection module).

The cartridge can be configured to provide closed-tube reactions after addition of the test sample. The cartridge can include one or more reagent chambers configured to contain any useful assay reagent, one or more ports configured to receive a sample, and one or more reaction chambers configured to contain the sample and the assay reagent(s). Such reagent chambers, ports, and reaction chambers can be connected to provide fluidic communication between such chambers and ports. Alternatively, the cartridge can include a single chamber configured to contain any useful assay reagent(s) and to receive a test sample.

The detection module may include a detector (e.g., an electronic detector, an optical detector, a cell phone camera, a photodiode, a laser-emitting diode, a photomultiplier tube, and/or a CCD camera) suitable for detecting a signal from one or more labels (e.g., for any probe described herein). The detector module may include, for example, a laser and optics suitable for optical detection of fluorescence from fluorescent labels. In other examples, other detectors, such as electronic detectors, may be used. The detection module can include any useful component, including an excitation source (e.g., configured to excite one or more labels present employed in the assay), an optical filter (e.g., a multipass filter), and/or an emission filter.

The processing module may be coupled to the heating module, the detection module, the motor module, and/or the network relay module. Furthermore, the processing module can be configured to provide one or more signals (e.g., one or more control signals to those modules and/or components), as well as to receive one or more signals (e.g., one or more electronic signals from the detection module corresponding to the presence or absence of a label). All or selected components or modules may be housed in a common housing or in separate enclosures (e.g., optionally configured to operate together, such as by providing a hinged housing formed by connecting an upper enclosure to a lower enclosure by use of a hinge).

The processing module may include one or more processing units, such as one or more processors. In some examples, the processing module may include a controller, logic circuitry, and/or software for performing functionalities described herein. The processing module may be coupled to one or more memories, input devices, and/or output devices including, but not limited to, disc drives, keyboards, mice, and displays. The processing module may provide control signals to the heating module, the detection module, the motor module, and/or network relay module.

The processing module may develop these control signals in accordance with input from an operator and/or in accordance with software. The software may include one or more executable instructions (e.g., stored on one or more memories) configured to cause the processing module to output a predetermined sequence of control signals, to perform one or more calculations (e.g., determine the presence or absence of a target based on electronic signals from the detection module), to communicate any useful output (e.g., a result, a setpoint, a level, etc.) over a network, to store any useful output in memory, and/or display any useful output on a display module. It is to be understood that the configuration of the processing module and related components is quite flexible, and any of a variety of computing systems may be used including server systems, desktops, laptops, controllers, smartphones, and the like.

Primer and Probe Design

The system of the invention can include any useful assay agent stored within the cartridge. Exemplary assay agents include a primer designed to hybridize to the target nucleic acid sequence, or portions thereof, as well as amplicons derived from the target nucleic acid sequence. Furthermore, the primer (e.g., any herein, such as an inner primer, outer primer, or loop primer) can be labeled with a fluorescent label (e.g., for use with a quench probe) or can be unlabeled (e.g., for use with a quench probe and a signal probe). The concentration of the primer and probes can be optimized to promote the amplification reaction and/or to promote signal discrimination after the amplification reaction is conducted. In some instances, the concentration of the quench probe is greater than the concentration of the primer to which the quench probe is designed to hybridize.

As described herein, the quench probe can be designed to have a $T_m$ that is lower than the temperature at which the amplification reaction is generally conducted (e.g., a $T_1$ of from about 55° C. to about 65° C.). In some instance, the $T_m$ of the quench probe is less than about 55° C. (e.g., of from about 10° C. to about 55° C., such as from 10° C. to 50° C., from 10° C. to 45° C., from 10° C. to 40° C., from 10° C. to 35° C., from 10° C. to 30° C., from 15° C. to 55° C., from 15° C. to 50° C., from 15° C. to 45° C., from 15° C. to 40° C., from 15° C. to 35° C., from 15° C. to 30° C., from 20° C. to 55° C., from 20° C. to 50° C., from 20° C. to 45° C., from 20° C. to 40° C., from 205° C. to 35° C., from 20° C. to 30° C., or from 20° C. to 25° C.). Such $T_m$ can be designed by shortening the length of the nucleic acid sequence (e.g., to any length described herein) and/or introducing one or more base mismatches (e.g., internal and/or terminal mismatches).

Additional details on primer design, RT-LAMP conditions, and LAMP conditions, are described in U.S. Pat. Nos. 6,410,278, 8,900,807, 9,074,243, 9,074,249, U.S. Pub. No. 2013/0171643, as well as Ball C S et al., "Quenching of unincorporated amplification signal reporters in reverse-transcription loop-mediated isothermal amplification enabling bright, single-step, closed-tube, and multiplexed detection of RNA viruses," *Anal. Chem.* 2016; 88(7):3562-8; Notomi T et al., "Loop-mediated isothermal amplification of DNA," *Nucleic Acids Res.* 2000 Jun. 15; 28(12):e63 (7 pp.); and Parida M et al., "Real-time reverse transcription loop-mediated isothermal amplification for rapid detection of West Nile virus," *J. Clin. Microbiol.* 2004 January; 42(1):257-63), each of which is incorporated herein by reference in its entirety.

The primers and probes herein can include any useful label, including fluorescent labels and quencher labels at any useful position in the nucleic acid sequence (e.g., at the 3'- and/or 5'-terminus).

Exemplary fluorescent labels include a quantum dot, a fluorophore), etc. Examples of fluorescence labels for use in this method includes fluorescein, 6-FAM™ (Applied Biosystems, Carlsbad, Calif.), TET™ (Applied Biosystems, Carlsbad, Calif.), VIC™ (Applied Biosystems, Carlsbad, Calif.), MAX, HEX™ (Applied Biosystems, Carlsbad, Calif.), TYE™ (ThermoFisher Scientific, Waltham, Mass.), TYE665, TYE705, TEX, JOE, Cy™ (Amersham Biosciences, Piscataway, N.J.) dyes (Cy2, Cy3, Cy3B, Cy3.5, Cy5, Cy5.5, Cy7), Texas Red® (Molecular Probes, Inc., Eugene, Oreg.), Texas Red-X, AlexaFluor® (Molecular Probes, Inc., Eugene, Oreg.) dyes (AlexaFluor 350, AlexaFluor 405, AlexaFluor 430, AlexaFluor 488, AlexaFluor 500, AlexaFluor 532, AlexaFluor 546, AlexaFluor 568, AlexaFluor 594, AlexaFluor 610, AlexaFluor 633, AlexaFluor 647, AlexaFluor 660, AlexaFluor 680, AlexaFluor 700, AlexaFluor 750), DyLight™ (ThermoFisher Scientific, Waltham, Mass.) dyes (DyLight 350, DyLight 405, DyLight 488, DyLight 549, DyLight 594, DyLight 633, DyLight 649, DyLight 755), ATTO™ (ATTO-TEC GmbH, Siegen, Germany) dyes (ATTO 390, ATTO 425, ATTO 465, ATTO 488, ATTO 495, ATTO 520, ATTO 532, ATTO 550, ATTO 565, ATTO Rho101, ATTO 590, ATTO 594, ATTO 610, ATTO 620, ATTO 633, ATTO 635, ATTO 637, ATTO 647, ATTO 647N, ATTO 655, ATTO 665, ATTO 680, ATTO 700, ATTO 725, ATTO 740), BODIPY® (Molecular Probes, Inc., Eugene, Oreg.) dyes (BODIPY FL, BODIPY R6G, BODIPY TMR, BOPDIPY 530/550, BODIPY 558/568, BODIPY 564/570, BODIPY 576/589, BODIPY 581/591, BODIPY 630/650, BODIPY 650/665), HiLyte Fluor™ (AnaSpec, Fremont, Calif.) dyes (HiLyte Fluor 488, HiLyte Fluor 555, HiLyte Fluor 594, HiLyte Fluor 647, HiLyte Fluor 680, HiLyte Fluor 750), AMCA, AMCA-S, Cascade® Blue (Molecular Probes, Inc., Eugene, Oreg.), Cascade Yellow, Coumarin, Hydroxycoumarin, Rhodamine Green™-X (Molecular Probes, Inc., Eugene, Oreg.), RhodamineRed™-X (Molecular Probes, Inc., Eugene, Oreg.), Rhodamine 6G, TMR, TAMRA™ (Applied Biosystems, Carlsbad, Calif.), 5-TAMRA, ROX™ (Applied Biosystems, Carlsbad, Calif.), Oregon Green® (Life Technologies, Grand Island, N.Y.), Oregon Green 500, IRDye® 700 (Li-Cor Biosciences, Lincoln, Nebr.), IRDye 800, WellRED D2, WellRED D3, WellRED D4, and Lightcycler® 640 (Roche Diagnostics GmbH, Mannheim, Germany). In some embodiments, bright fluorophores with extinction coefficients >50,000 $M^{-1}$ $cm^{-1}$ and appropriate spectral matching with the fluorescence detection channels can be used.

In a specific embodiment, a fluorescently labeled primer is included in a reaction mixture and a fluorescently labeled reaction product is produced. Fluorophores used as labels to generate a fluorescently labeled primer included in embodiments of methods and compositions of the present invention can be any of numerous fluorophores including, but not limited to, those described in Haughland, R. P., The Handbook, A Guide to Fluorescent Probes and Labeling Technologies, 10th Ed., 2005; Lakowicz, J. R., Principles of Fluorescence Spectroscopy, Springer, 3rd ed., 2006; 4-acetamido-4'-isothiocyanatostilbene-2,2' disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcoumarin (Coumaran 151); cyanosine; DAPDXYL sulfonyl chloride; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene- 1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), hexachlorofluorescenin, 5-(4,6-dichlorotriazin-2-yl)aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl} amino) naphthalene-1-sulfonic acid), Malachite Green isothiocyanate; 4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), 6-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N', N-tetramethyl-carboxyrhodamine (TAMRA); tetramethyl rhodamine; tetramethyl rhodamine isothiocyanate (TRITC); riboflavin; rosolic acid and terbium chelate derivatives.

Exemplary quencher labels include a fluorophore, a quantum dot, a metal nanoparticle, etc.). Suitable quenchers include Black Hole Quencher®-1 (Biosearch Technologies, Novato, Calif.), BHQ-2, Dabcyl, Iowa Black® FQ (Integrated DNA Technologies, Coralville, Iowa), IowaBlack RQ, QXL™ (AnaSpec, Fremont, Calif.), QSY 7, QSY 9, QSY 21, QSY 35, and IRDye QC. In one instance, the term "quencher" refers to a substance which reduces emission from a fluorescent donor when in proximity to the donor. Fluorescence is quenched when the fluorescence emitted from the fluorophore is detectably reduced, such as reduced by 10%, 20%, 30%, 40%, 50%, 60%, 70%, 80%, 90%, 95%, 99% or more. Numerous fluorophore quenchers are known in the art, including, dabcyl; sulfonyl chlorides such as dansyl chloride; and Black Hole Quenchers BHQ-1, BHQ-2, and BHQ-3.

Any detection method or system operable to detect a labeled reaction product can be used in methods according to embodiments of the present invention and such appropriate detection methods and systems are well-known in the art. A signal from the fluorescently labeled reaction product is detected, for instance, using a UV light source, a LED light source, a flashlight, etc., such as from a mobile device or a smartphone.

Additional examples of fluorophore/quencher pairs are known in the art, for instance, described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005, which is incorporated herein by reference in its entirety.

Various embodiments of the assays and methods include use of one or more enzymes (e.g., a strand displacement polymerase or an archeal polymerase), including a plurality of polymerases. If the target nucleic acid includes a RNA sequence, or a portion of an RNA sequence, then a reverse transcriptase can be employed to reverse transcribe the RNA target into a DNA (e.g., cDNA) sequence.

Exemplary enzymes include Bst DNA polymerase, Bca (exo-)DNA polymerase, DNA polymerase I Klenow fragment, Vent DNA polymerase, Vent (exo-)DNA polymerase (Vent DNA polymerase deficient in exonuclease activity), Vent™ DNA polymerase, 9° N™ polymerase, Deep Vent DNA polymerase, Deep Vent(exo-)DNA polymerase (Deep Vent DNA polymerase deficient in exonuclease activity), 129 phage DNA polymerase, MS-2 phage DNA polymerase, Z-Taq DNA polymerase (Takara Shuzo Co., Ltd.), Taq polymerase, and KOD DNA polymerase (Toyobo Co., Ltd.), as well as variants thereof, such as Bst 2.0 or Bst 2.0 WarmStart™ DNA polymerases (New England Biolabs, Ipswich, Mass.) and combinations thereof (e.g., a blend of a strand displacement polymerase and Taq (see for example, OneTaq, New England Biolabs, Ipswich, Mass.)).

Multiplexing

The methods, probes, primers, and assays described herein are amenable to high-plex amplification. Multiplexing of samples and detection of amplification products can be achieved in a single reaction vessel as described herein. If desired, size determination can be performed by means of downstream analysis including capillary electrophoresis, which separates products based on size and can detect fluorescent labels.

Additional Components

The present system (e.g., cartridge) can include one or more additional components, as described herein. For instance, one or more detection components can be provided, which can allow for detection by electrochemical, colorimetric, fluorescent, western blot, immunohistochemistry, immunoassay (e.g., lateral flow assay), immunochromatography, radio immunoassay, optical immunoassay, enzyme immunoassay, and chemiluminescence, and/or electrochemiluminescence methods in any useful format.

The device can include one or more separation/extraction components (e.g., filters, posts, membranes, weirs (optionally including beads), matrices, or high voltage electrodes for performing on-chip capillary electrophoresis separations); heating components (e.g., electrodes or filaments); pumps (e.g., active or passive pumps, such as a low flow rate peristaltic pump or application of negative pressure, such as by actuating a valve); a membrane (e.g., placed within a channel and/or a chamber); a multifunctional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an actuator; a wireless power coil; a device for radio frequency (RF) communications (e.g., such as high-frequency inductors, capacitors, oscillators, and antennae); a resistance-based temperature sensor; a photodetector; a photovoltaic cell; a diode; a data-processing circuit powered by the power source and electrically connected to the energy source; and/or one or more components for autonomous remote monitoring of a sample, such as an analog-to-digital converter, a radiofrequency module, and/or a telemetry unit (e.g., configured to receive processed data from a data-processing circuit electrically connected to the detection component and to transmit the data wirelessly).

Methods of Use

The present system and/or cartridge can be integrated with any assay for detecting any target of interest (e.g., any described herein). In particular, the cartridge of the invention is disposable, thereby facilitating single-use detection of samples that could be easily contaminated or could be potentially hazardous (e.g., infectious). In some embodiments, the cartridge is configured for sensing a nucleic acid (e.g., DNA or RNA), as well as for detecting a pathogen (e.g., a bacterial pathogen, a viral pathogen, such as any herein), metabolite, genetic modification, and/or pesticide for any use (e.g., livestock monitoring, crop maintenance, as well as any other agricultural use). Exemplary uses include any useful methodology for detection a target (e.g., any described herein), such as polymerase chain reaction amplification, cell culture techniques, etc.

Targets and Samples

The present system can be used to detect any useful targets (e.g., a target nucleic acid or a nucleic acid sequence derived from the target or identifiable as the target). Exemplary targets include a bacterium, such as such as *Bacillus* (e.g., *B. anthracis*), Enterobacteriaceae (e.g., *Salmonella, Escherichia coli, Yersinia pestis, Klebsiella,* and *Shigella*), *Yersinia* (e.g., *E. pestis* or *E. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis,* or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii,* or *R. typhi*), *Francisella tularensis, Chlamydia psittaci, Coxiella burnetii, Mycoplasma* (e.g., *M. mycoides*), etc.; an allergen, such as mycotoxins, mold spores, or bacterial spores such as *Clostridium botulinum* and *C. perfringens*; a toxin, such as ricin, mycotoxin, tetrodotoxin, anthrax toxin, botulinum toxin, staphylococcal entertoxin B, or saxitoxin; a virus, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania,* or *Trypanosoma* (e.g., *T. brucei* and *T. cruzi*); a helminth, such as cestodes (tapeworms), trematodes (flukes), or nematodes (roundworms, e.g., *Ascaris lumbricoides, Trichuris trichiura, Necator americanus,* or *Ancylostoma duodenale*); a parasite (e.g., any protozoa or helminths described herein); a fungus, such as Aspergilli, Candidae, *Coccidioides immitis,* and Cryptococci; a pathogen; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene of any useful pathogen, such as those described herein); or a genetic modification (e.g., antibiotic resistance marker gene). Targets also include food-borne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni,* and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum,* Variola (e.g., *V. major*), Filoviridae (e.g., Ebola virus and Marburg virus), Arenaviridae (e.g., Lassa virus and Machupo virus), *Clostridium perfringens,* any food-borne pathogen (e.g., *Salmonella* species, *Escherichia coli* O157: H7, or *Shigella*), *Chlamydia psittaci, Coxiella burnetii, Staphylococcal aureus, Rickettsia* (e.g., *R. prowazekii* or *R. rickettsii*), Alphavirus (e.g., Venezuelan equine encephalitis virus, eastern equine encephalitis virus, or western equine encephalitis virus), *Vibrio cholerae, Cryptosporidium parvum,* Henipavirus (e.g., Nipah virus), Bunyaviridae (e.g., Hantavirus or Rift Valley fever virus), Flaviviridae (e.g., Japanese encephalitis virus and Yellow fever virus), and *Coccidioides* spp.

The test sample can include any useful sample, such as a microorganism, a virus, a bacterium, a fungus, a parasite, a helminth, a protozoon, a cell, tissue, a fluid, a swab, a biological sample (e.g., blood, serum, plasma, saliva, etc.), a plant, an environmental sample (e.g., air, soil, and/or water), etc. Such samples can include any useful matrix (e.g., stabilized matrix, such as any described herein).

Label Agents and Capture Agents

A label agent includes any moiety that can emit a signal suitable for detection, such as an optical or an electrical signal. The label agent can optionally include a capture portion, which binds to a target or a portion thereof. Furthermore, a label agent can be used in conjunction with a capture agent (e.g., as in a sandwich assay, which can include use of a capture agent to bind a first region of the target to a bead and use of a label agent to bind to a second region of the target in order to provide a detectable signal).

Exemplary capture agents include a protein that binds to or detects one or more markers (e.g., an antibody or an enzyme), an affibody, an aptamer, a globulin protein (e.g., bovine serum albumin), a nanoparticle, a microparticle, a sandwich assay reagent, a nucleic acid (e.g., single stranded nucleic acid, double stranded nucleic acid, hairpin nucleic acid, DNA, RNA, cell-free nucleic acids, as well as chimeras thereof, hybrids thereof, or modifications thereof), a toxin capture agent (e.g., a sarcin-ricin loop capture agent), a major histocompatibility complex capture agent (e.g., a MHC II capture agent), or a catalyst (e.g., that reacts with one or more markers.

Exemplary label agents include a capture agent (e.g., any herein), a detectable molecule or compound (e.g., a probe (e.g., a fluorescence resonance energy transfer or FRET probe, a fluorescent probe, and/or a quencher probe), an electroactive label, an electrocatalytic label, a fluorescent label, a fluorogenic substrate (e.g., a non-fluorescent substrate capable of being activated to produce a detectable fluorescent signal), a chromogenic label, a chromogenic substrate (e.g., a non-chromogenic substrate capable of being activated to produce a detectable chromogenic signal), a colorimetric label, a quantum dot, a particle, a nanoparticle, a microparticle, a barcode, a radio label (e.g., an RF label or barcode), a magnetic label, a magnetic field sensor active label (e.g., a giant magneto resistive (GMR) sensor label or an anisotropic magnetoresistor (AMR) sensor label), a spin label, an electron resonance active label (e.g., an electron paramagnetic resonance (EPR) active label of an electron spin resonance (ESR) active label), avidin, biotin, a tag, a dye, a marker, an enzyme that can optionally include one or more linking agents and/or one or more dyes, etc.), or a combination of a capture agent with a detectable molecule or a detectable compound. Other exemplary label agents include nucleic acid dyes, lipid dyes, etc.

The capture agent can include any useful reactive group (e.g., a functional group that is one of a cross-linker group, a binding group, or a click-chemistry group, such as any described herein). Exemplary reactive groups include any chemical group configured to form a bond. In general, a first chemical group reacts with a second chemical group to form a bond (e.g., a covalent bond), in which the first and second chemical groups form a reactive pair.

In one instance, the reactive group is a cross-linker group. In another non-limiting instance, the reactive pair is a cross-linker reaction pair, which includes a first cross-linker group and a second cross-linker group that reacts with that first cross-linker group. Exemplary cross-linker groups and cross-linker reaction pairs include those for forming a covalent bond between a carboxyl group (e.g., $CO_2H$) and an amino group (e.g., $NH_2$); or between a phospho group (e.g., $P(O)(OH)_2$) and an amino group (e.g., $NH_2$), such as 1-ethyl-3-(3-dimethylaminopropyl)carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., $NH_2$) and a thymine moiety, such as succinimidyl-[4-(psoralen-8-yloxy)]-butyrate (SPB); a hydroxyl group (e.g., OH) and a sulfur-containing group (e.g., free thiol, SH, sulfhydryl, cysteine moiety, or mercapto group), such as p-maleimidophenyl isocyanate (PMPI); between an amino group (e.g., $NH_2$) and a sulfur-containing group (e.g., free thiol, SH, sulfhydryl, cysteine moiety, or mercapto group), such as succinimidyl 4-(p-maleimidophenyl)butyrate (SMPB) and/or succinimidyl 4-(N-maleimidomethyl)cyclohexane-1-carboxylate (SMCC); between a sulfur-containing group (e.g., free thiol, SH, sulfhydryl, cysteine moiety, or mercapto group) and a carbonyl group (e.g., an aldehyde group, such as for an oxidized glycoprotein carbohydrate), such as N-beta-maleimidopropionic acid hydrazide-trifluoroacetic acid salt (BMPH), 3-(2-pyridyldithio)propionyl hydrazide (PDPH), and/or a 3-(2-pyridyldithio)propionyl group (PDP); between a maleimide-containing group and a sulfur-containing group (e.g., free thiol, SH, sulfhydryl, cysteine moiety, or mercapto group); between a sulfur-containing group (e.g., free thiol, SH, sulfhydryl, cysteine moiety, or mercapto group) and an alkene group or an alkyne group; between a reactive carbene group (e.g., arising from photoactivation of a diazirine group) and a functional group having an active hydrogen group (e.g., as in an alkene group) and/or a nucleophilic group (e.g., as in a leaving group); and between a reactive nitrene group (e.g., arising from photoactivation of an aryl azide group) and a functional group having an active hydrogen group (e.g., as in an alkene group) and/or a nucleophilic group (e.g., as in a leaving group). Yet other cross-linkers include those for forming a covalent bond between two or more unsaturated hydrocarbon bonds, e.g., mediated by radical polymerization, such as a reaction of forming a covalent bond between a first alkene group and a second alkene group (e.g., a reaction between acrylate-derived monomers to form a polyacrylate, polyacrylamide, etc.). Other cross-linkers include those having photoactivatable groups, which upon photoreaction produces a reactive intermediate (e.g., such as cross-linkers including a benzophenone moiety, a diazirine moiety, or an aryl azide moiety).

In another instance, the reactive group is a binding group. In another non-limiting instance, the reactive pair is a binding reaction pair, which includes a first binding group and a second binding group that reacts with that first binding group. Exemplary binding groups and binding reaction pairs include those for forming a covalent bond between biotin and avidin, biotin and streptavidin, biotin and neutravidin, desthiobiotin and avidin (or a derivative thereof, such as streptavidin or neutravidin), hapten and an antibody, an antigen and an antibody, a primary antibody and a secondary antibody, lectin and a glycoprotein, and a nucleic acid and a complement thereof.

In yet another instance, the reactive group is a click-chemistry group. In another non-limiting instance, the reactive pair is a click-chemistry reaction pair, which includes a first click-chemistry group and a second click-chemistry group that reacts with that first click-chemistry group. Exemplary click-chemistry groups include, e.g., a click-chemistry group, e.g., one of a click-chemistry reaction pair selected from the group consisting of a Huisgen 1,3-dipolar cycloaddition reaction between an alkynyl group and an azido group to form a triazole-containing linker; a Diels-Alder reaction between a diene having a $4\pi$ electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and a dienophile or heterodienophile having a $2\pi$ electron system (e.g., an optionally substituted alkenyl group or an optionally substituted alkynyl group); a ring opening reaction with a nucleophile and a strained heterocyclyl electrophile; and a splint ligation reaction with a phosphorothioate group and an iodo group; and a reductive amination reaction with an aldehyde group and an amino group.

Other Reagents

The present cartridge can be configured for use with any number of reagents either on-chip and/or off-chip. Exemplary reagents include a lysing agent (e.g., a detergent, such as saponin); a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; an antibiotic; a catalyst; an enzyme; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, a coated particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer (e.g., for binding to a selective region of the target nucleic acid)), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a buffer (e.g., a phosphate or borate buffer, which can optionally include one or more salts, kosmotropes, and/or chaotropes), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

The assay can be conducted in the presence of one or more stabilizing agents (e.g., provided on-chip within a cartridge). Exemplary stabilizing agents include one or more chelators (e.g., chelators for one or more metal ions, which can decompose one or more sterilization agents, such as an aromatic amine), detergents, surfactants (e.g., a nonionic, cationic, or anionic surfactant), alkaline agents (e.g., urea), preservatives (e.g., ethylenediamine tetra acetic acid compounds), scavenging agents (e.g., free radical scavenging agents, such as diarylamines or substituted dihydroquinolines), sequestrants (e.g., organic phosphonic acid), stabilizers (e.g., pyrophosphate, pyrophosphoric acid, dipicolinic acid, acetic acid, propionic acid, sulfonates, sulfates, phosphates, organic peroxycarboxylic acid, a stannate compound, organic phosphonic acids, amine-substituted phosphonic acids, alkyleneaminomethylene phosphonic acids, carboxylic acid substituted N-containing heterocyclics, aminopolycarboxylic acids, polyaminocarboxylic acids, tin-based compounds, phosphoric acids, alkylbenzene sulfonates with 6-18 carbon atoms, alkyl sulfates, and water-soluble salts of these acids), and/or buffers to inhibit or reduce decomposition of the sterilization agent.

In other embodiments, a stabilizing agent can be combined with an assay agent and provided in a form that increases storage life. Such forms include powder, granule, pellet, gel, lyophilized, freeze-dried, and/or foam forms of the assay agent. Such forms can optionally include one or more chelators, detergents, surfactants, alkaline agents, preservatives, scavenging agents, sequestrants, stabilizers, and/or buffers, such as any described herein.

EXAMPLES

Example 1: Smart Trap—An Integrated Microfluidic System Enabling Real-Time Autonomous Field Surveillance for Vector-Borne Pathogens We report for the first time on a fully integrated, portable, and inexpensive microfluidic chip and chip-handling robot that can be deployed in a network to enable real-time autonomous field surveillance for vector-borne pathogens over an arbitrarily sized geographic region. Our system attracts mosquitos to feed on sugar baits and then analyze mosquito saliva using reverse transcription loop mediated isothermal amplification (RT-LAMP) to detect a panel of mosquito-borne viruses, including West Nile virus, chikungunya virus, and Zika virus. Here, we discuss the features of the microfluidic chip and autonomous chip handling robot. Our device utilizes isothermal nucleic acid amplification, coupled to a novel DNA-based detection method, to selectively and specifically detect RNA viruses from mosquito saliva deposited onto solid or liquid sugar baits. The chip handling, robotic "smart trap", enables daily, autonomous sample processing and wireless result reporting to a biosurveillance ecosystem, where predictions of disease transmission risk can be made on a daily, spatially resolved basis.

Around the world, vector-borne RNA viruses present an acute threat to people and economically important livestock in the form of zoonotic outbreaks or agents of bioterrorism. Many of these viruses lack effective vaccines and therapies, leaving proactive vector surveillance and control as the only effective strategy for preventing disease outbreaks. Current methods of biosurveillance require specially trained mosquito biologists to collect, sort, and test thousands of mosquitoes by hand for a limited number of agents. This process is slow, laborious, expensive, and lacks high temporal and spatial resolution. Our work differs from that of vector control agencies because we integrate the bait presentation and regular molecular testing, analysis, and data storage into an automated microfluidic system and connected network of traps.

We designed the microfluidic chip (FIG. 1) to minimize the need for actuation and eliminate the risk of system contamination. The chip is made from acrylic by conventional machining, with the potential for mass production by injection molding. A thin acrylic backing is bonded to the chip using a chloroform-vapor assisted thermal bonding technique capable of withstanding at least 40 PSI at 70° C. for 1 hour. Passive, normally closed microfluidic check valves with adjustable opening pressures (from 1 to 40 PSI) and no backflow are installed using an interference fit. Exemplary microfluidic check valves are described in, e.g., Ball C S et al., "A simple check valve for microfluidic point of care diagnostics," *Lab Chip* 2016; 16(22):4436-44.

An elastic EPDM membrane is glued to the chip using cyanoacrylate to create an onboard reagent storage reservoir. The chip's channel geometries allow for dry-storage of all RT-LAMP assay reagents into 8 parallel reaction channels 1 MS2 phage positive assay control, 1 negative control, and 6 test channels using a vacuum centrifuge. Other configurations of channels are possible. After desiccation, channel fill and vent holes are sealed off with press-fit plug strips that create a gas-tight seal.

The chip's conical feeding well presents either liquid or solid sugar baits to mosquitos, which are attracted to the bait by a floral scent. The use of sugar baits to detect mosquito-borne viruses has been reported previously (see, e.g., Lothrop H D et al., "Use of scented sugar bait stations to track mosquito-borne arbovirus transmission in California," *J. Med. Entomol.* 2012; 49(6):1466-72) but trap setting, analysis, and result reporting were manual and took weeks for turnaround. The conical feeding well can optionally include the bait (e.g., liquid or solid baits) with an assay reagent (e.g., a pellet of dry-stabilized enzyme and/or deoxyribonucleotides (dNTPs) for a RT-LAMP assay).

Pressing on the chip's EPDM membrane dispenses onboard rehydration buffer (e.g., fluid containing salts and components for an assay reaction) or liquid bait solution into the feeding well through a check valve. Once the bait is rehydrated and fed upon, a spinning magnet in the robotic handler rotates a stainless steel ball bearing in the feeding well to mix the sample. The sample is then passed through another check valve and through a flow splitter to rehydrate dried assay reagents (e.g., dehydrated or dried primers for a QUASR RT-LAMP assay, such as one primer set for each reaction channel; or a control (e.g., no enzyme control or no-quencher control for setting QUASR positive and negative control thresholds)). As fluid fills the chip, pressure builds inside of cylindrical air pockets positioned at the ends of each reaction channel. When the internal pressure reaches the fill pressure, the channels stop filling. Once the fill pressure is released, the check valve holds the reagents in place within the chip, preventing contamination of the chip handler. In one non-limiting instance, the cartridge includes a single large, shared pocket of air. Additional optimization may be possible, e.g. the current design with long and skinny channels might be replaced with wider, deeper channels of equivalent volume to allow greater path length for signal integration, and a lower surface-to-volume ratio to improve assay performance.

Figure 2A:
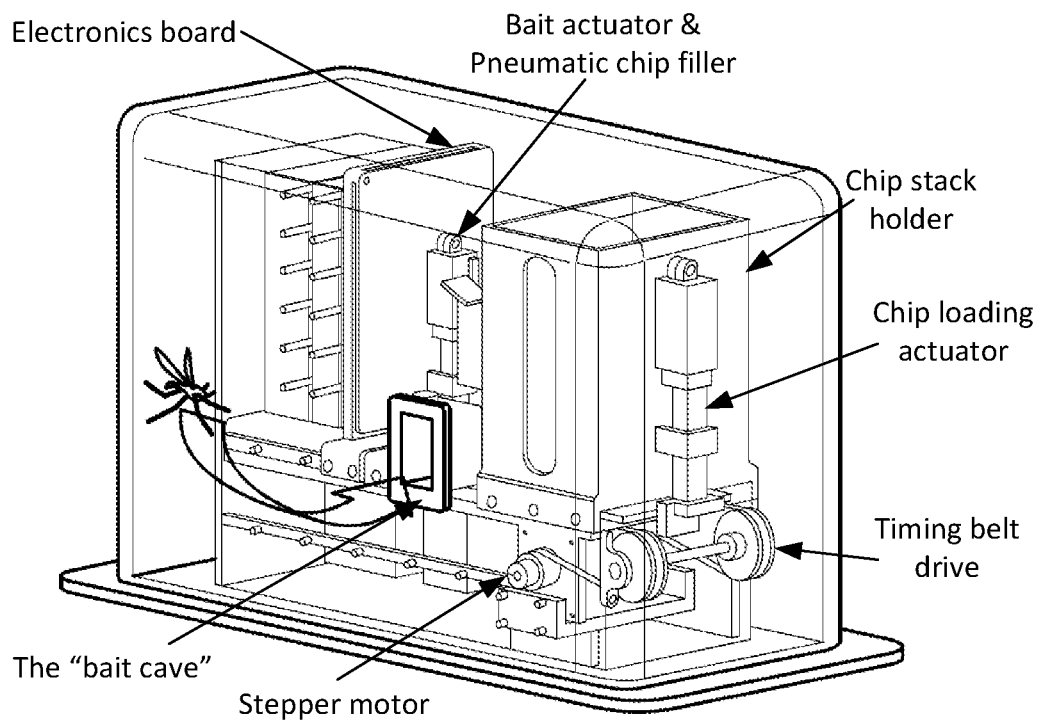
FIG. 2A-2C shows an exemplary system. Provided is (A) a schematic rendering of chip-handling robot. The smart trap is equipped with all the necessary components to store and process chips every day for 1 month. Also provided is (B) an image of a prototype device with battery and electronics board removed to show the chip over the heater and detector. Electronics shown here have been replaced with a single board mounted as in (A). Also provided is (C) a side view of a prototype with labeled components.
Figure 2B:
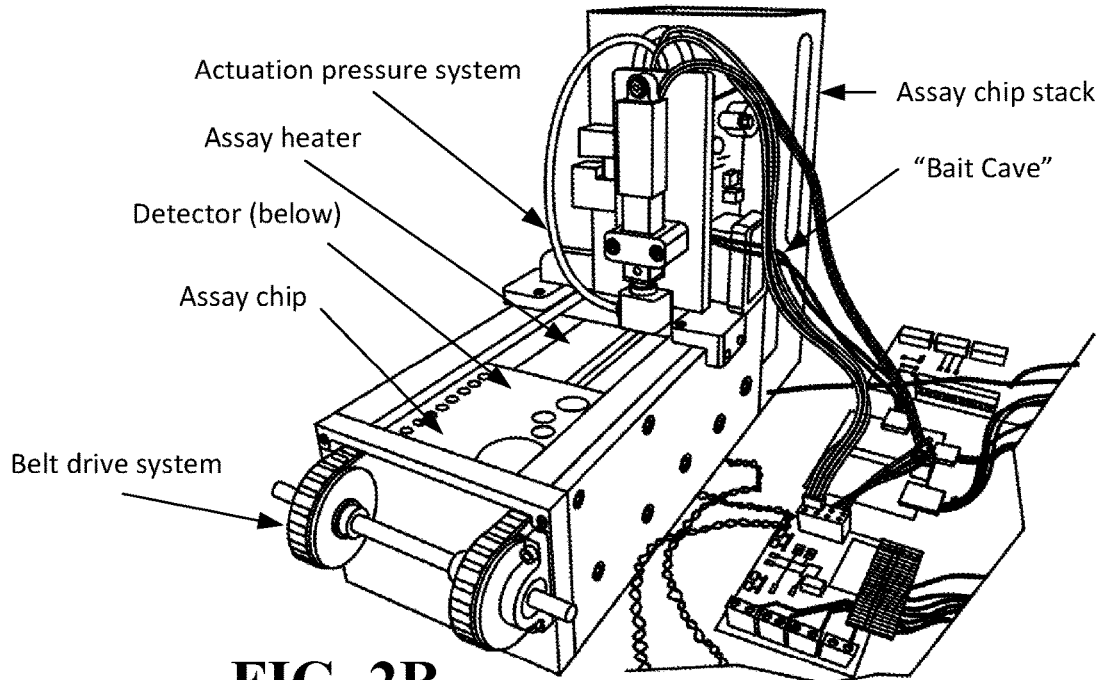
Figure 2C:
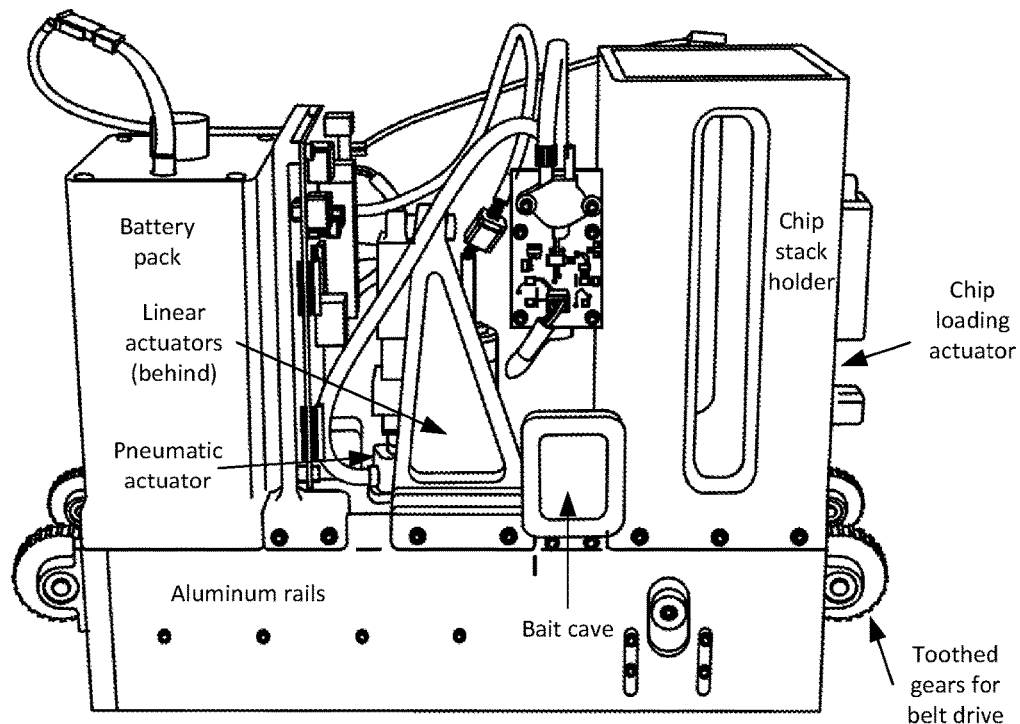

We built the chip handling robot (FIG. 2A-2C) out of both off-the-shelf and custom parts made by machining or 3D printing. The smart trap loads one chip daily from a stack of chips that enable autonomous operation for 1 month. A stepper motor drives a timing belt that engages with teeth on the microfluidic chip to move the chip through different stations in the trap. Servo motors are used to dispense fluid from the onboard fluid reservoir and create a face seal for pneumatic chip filling. A small DC pump connected to an air reservoir with a controlled leak provides the pressure needed to fill the chip with sample reagents (e.g., up to 25 PSI).

A spring-mounted heater with feedback control maintained the chip at a stable 65° C. for the 30 minute RT-LAMP reaction (see, e.g., Ball C S et al., *Anal. Chem.* 2016; 88(7):3562-8).

Figure 3A:
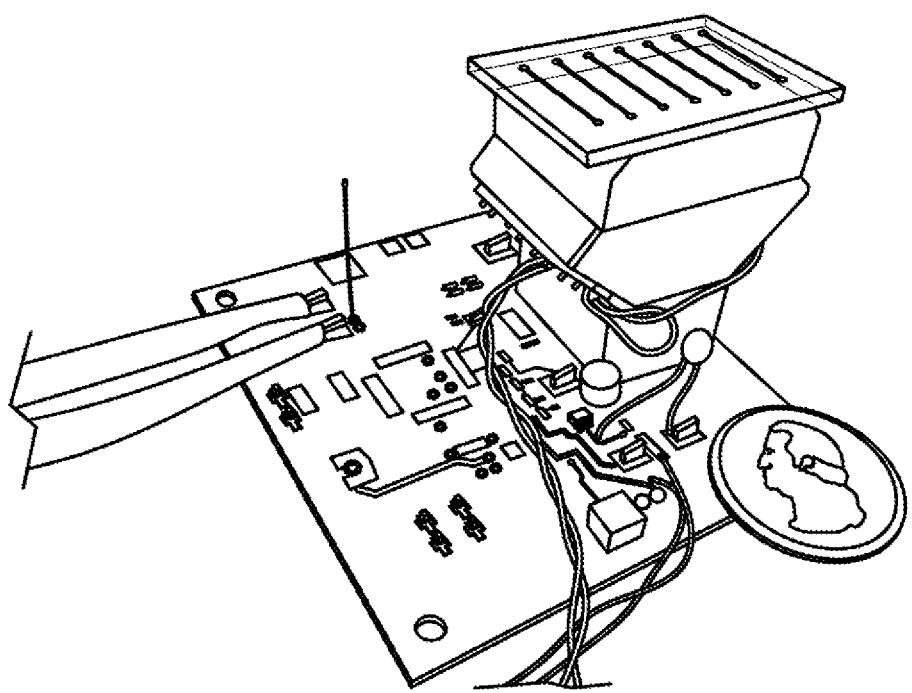
FIG. 3A-3B shows an exemplary detector module. Provided is (A) an image of a photodiode detector module, equipped with green light emitting diodes (LEDs) and colored plastic gel filters. Inexpensive optics can be integrated into a 3D printed part. A small plastic chip is shown for illustration of how channels align with detector. Also provided is (B) a detector scan of an 8-channel assay chip, illustrating discrimination between positive and negative channels and comparison to a threshold (dashed line). Data were obtained using a real chip and assay reagents.
Figure 3B:
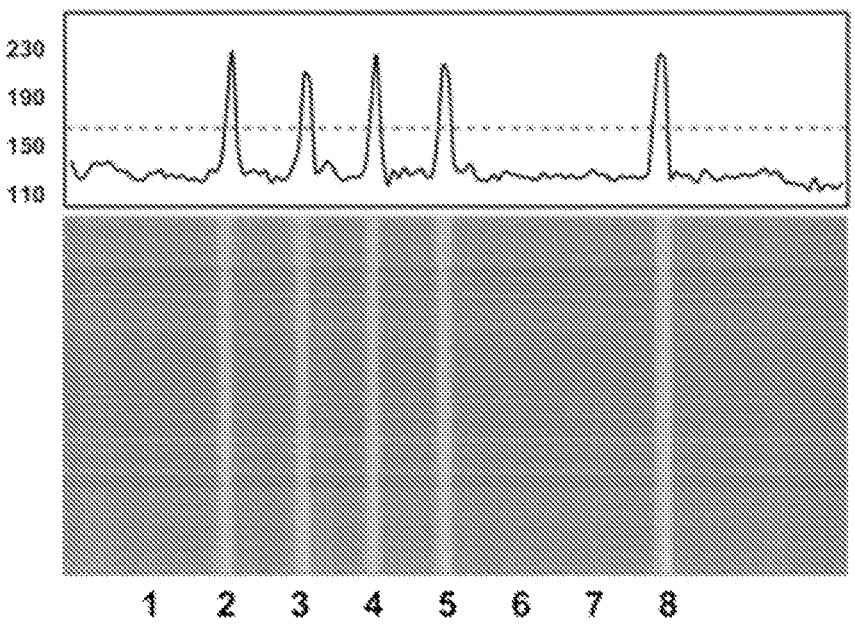

Once the chip cools, an inexpensive fluorometer made from LEDs, a linear diode array, and plastic theater lighting gels for excitation and emission filters determines whether RT-LAMP reactions are positive or negative (FIG. 3A-3B). The entire assembly is powered by a battery, which can be recharged with a small solar panel charger.

Figure 4:
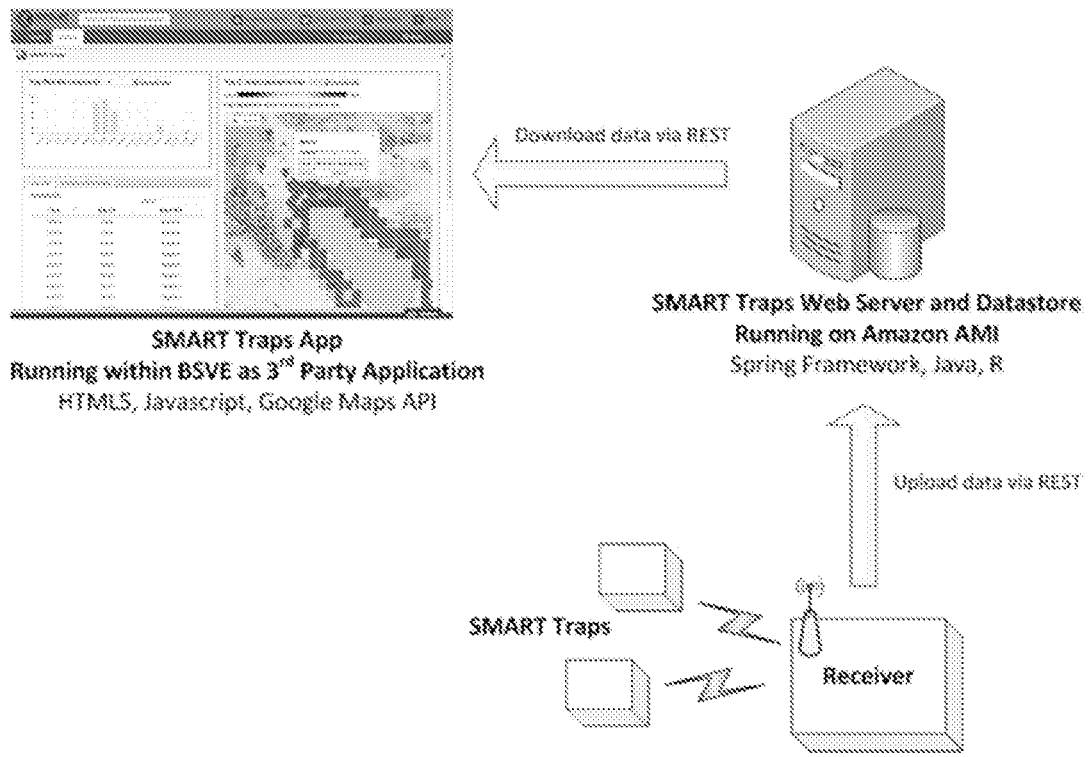
FIG. 4 shows a schematic of an exemplary networked trap communication. Smart Traps can communicate by a radio module to a receiver trap, which uploads data to a cloud service. The data can then be downloaded into a custom application that displays testing data over a mapping service.

The traps relay data through a network using Xbee to a mother-trap, which uploads daily test results to the cloud with a smartphone via text message (FIG. 4). Once the data is online, a simple algorithm scores assays as positive or negative for the virus targets and updates a web-based application with real-time biosurveillance data, available for analysts to use in the biosurveillance ecosystem. The web-based application also incorporates predictive modeling of disease risk, based on a combination of conventional vector surveillance (mosquito abundance and viral incidence based on $CO_2$-baited traps), and environmental/climatological models. In the future, the models can be adapted to provide risk maps based on viral incidence measured by the Smart Trap.

The communication architecture of the network relay module can be implemented with any useful electronics board (e.g., a main electronics board including a microprocessor for coordinated operation of subsystems) and have any useful links (e.g., three communication links include a first link that is a coordinator radio link to enable all Smart Traps to communicate among themselves, such as through a wireless mesh; a second link to enable transmission of acquired data from the coordinator radio link to an internet-accessible device (e.g., a smartphone); and a third link to enable communication of the acquired data from the internet-accessible device to a data management system, such as a cloud-based service system). To enable radio links between Smart Traps, each Smart Trap can include, e.g., a radio module (such as a local XBee radio module and a MSP430 microcontroller), to facilitate communication between each Smart Trap and communication to the coordinator radio module of a receiver (e.g., including a coordinator XBee radio module, an ATmega microcontroller, and a transmitter, such as a Bluetooth transmitter, to provide parsed, scored incoming data from Smart Traps to the data management system in any useful packaged form, such as a HTTP postpacket).

In one non-limiting embodiment, the subsystems or stations of the Smart Trap include the following: a chip stack that can hold up to a plurality of assay cartridges (e.g., 30 assay cartridges or assay chips); a chip loading actuator that can raise or lower the chip stack, allowing the bottom-most chip to mesh with the belt drive; a motion control system, such as a "timing belt" driven by a stepper motor, that engages the "teeth" features on the chip, with a series of opto-interrupts to determine chip positioning, and capable of stopping the chip at desired stations (e.g., optionally including reflective paint or reflective tape on a chip to improve the detection of chip edges); a "bait cave" in which the chip is positioned near a "portal" into which mosquitoes can enter, and have access to the scented sugar bait; a linear actuator that depresses on the fluid reservoir to dispense reaction buffer through the first check valve, into the feeding well (after the feeding period) to dissolve the bait with any deposited pathogen (e.g., virus), along with the enzyme pellet; a magnetic mixing station, in which a rotating magnet is used to spin a spherical magnetic ball bearing within the feeding reservoir, to assist in dissolving the bait and enzyme pellet in the reaction buffer; and/or a second linear actuator fitted with a pneumatic system to pressurize the headspace above the reservoir, thereby pushing fluid from the feeding well into the assay channels.

The subsystems or stations of the Smart Trap can also include, e.g., a heater capable of performing the isothermal incubation at 65° C. for 30 minutes. The heater can be machined from an aluminum block with a cartridge heating element and a temperature sensor (e.g., a resistance temperature detector (RTD)), and is mounted with springs to ensure a tight fit against the chip. The aluminum block can be machined with a sloped front so that as a chip advances, it slides over the heater, and then the springs hold the heater in place against the chip. The heater can be calibrated for setpoint versus internal chip temperature, and found to have a small offset (1-2° C.) at the assay temperature of 65° C.

The subsystems or stations of the Smart Trap can also include, e.g., a fluorescence detector including a bank of LEDs for excitation, a linear photodiode array for detection, with appropriate colored filters for fluorescence. The chip (after incubation) can be stepped past the detector to collect a series of "line scans," which can be built up to form a fluorescence intensity image for the chip (see, e.g., FIG. 3A-3B)

The subsystems or stations of the Smart Trap can also include electronics, e.g., an integrated system control board containing controllers for all subsystems (motors, actuators, heaters, etc.), as well as microprocessor for data processing, wireless networking via radio modules (e.g., Xbee), and state-of-health processing. The subsystems or stations of the Smart Trap can also include a power source, e.g., a lithium ion battery pack with an optional solar panel charger and a charging circuit.

There are numerous possible design improvements to the system described here, or even completely different configurations of systems that could be used for the purpose of performing an automated viral detection assay on baits. One variation would include housing a device like the smart trap inside of a larger container that collects mosquitoes and holds them "captive" for hours or days, increasing the likelihood that they will take a sugar meal. Other variations include different attraction strategies (e.g., addition of $CO_2$).

Example 2: Assay Cartridge

Figure 5:
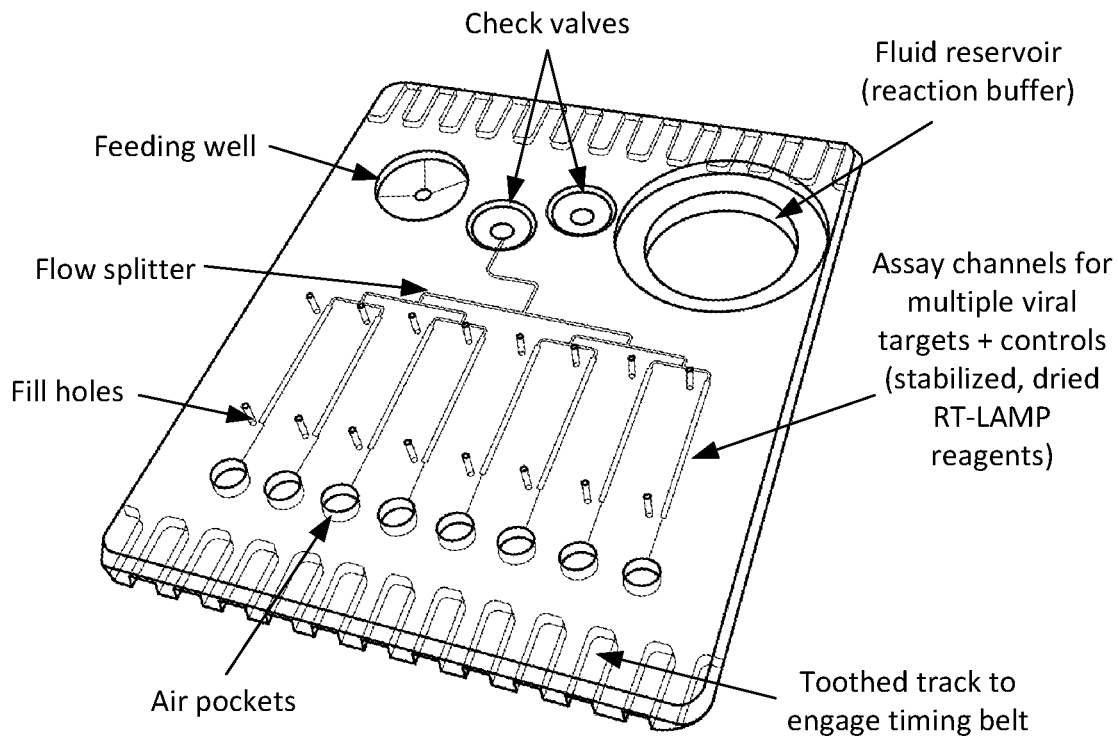
FIG. 5 shows an exemplary assay chip, which can be optionally configured to conduct RT-LAMP viral assays.

Any useful cartridge can be employed with the system, including one configured to conduct any useful assay (e.g., a viral amplification assay). FIG. 5 provides an exemplary cartridge (e.g., machined from PC or PMMA, in which scale-up can be accomplished by injection molding). The cartridge includes a feeding well configured to collect a test sample from an organism (e.g., optionally including an agent to attract an organism, e.g., such as a sugar bait for a mosquito), one or more check valves (e.g., unidirectional check valves configured to deliver the test sample to the one or more assay channels), one or more assay channels including agent(s) configured to conduct an assay for detecting a target (e.g., a target nucleic acid, such as any described herein, including those indicative of a viral and/or bacterial pathogen), and a machined track to engage a timing belt (e.g., for a motor module).

Figure 6:
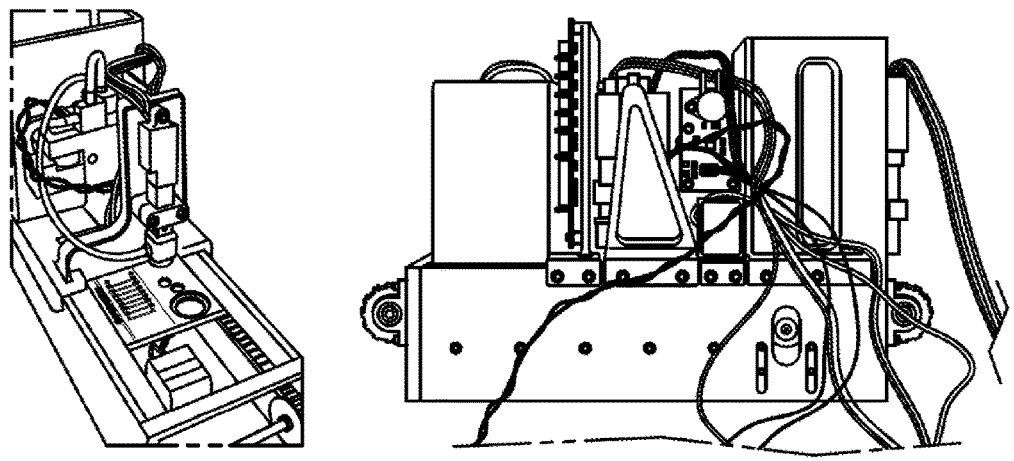
FIG. 6 shows photographs of chip at filling station including a top view (left) and side view (right).

Reagents can be filled in any useful manner (see, e.g., FIG. 6). The cartridges, once assembled, can be integrated into a holder (e.g., a stack or a carousel), which in turn can be housed within the Smart Trap system.

Example 3: An Exemplary Smart Trap System

Figure 7:
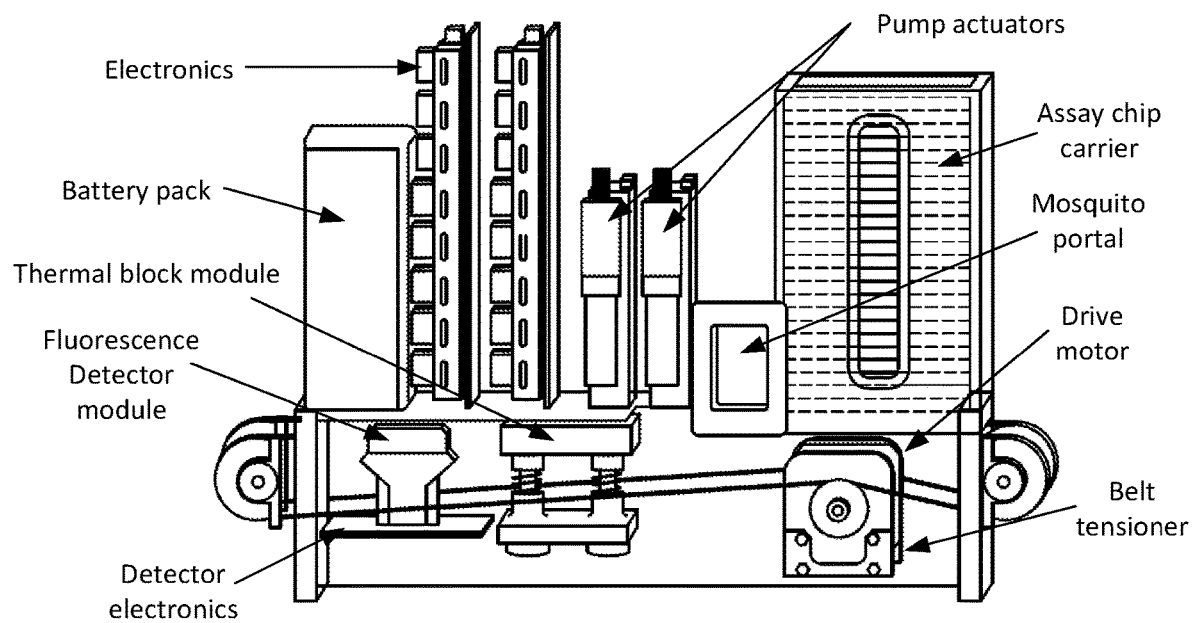
FIG. 7 shows an exemplary schematic of the Smart Trap system, in which system cover and side covers are removed for illustration.
Figure 8:
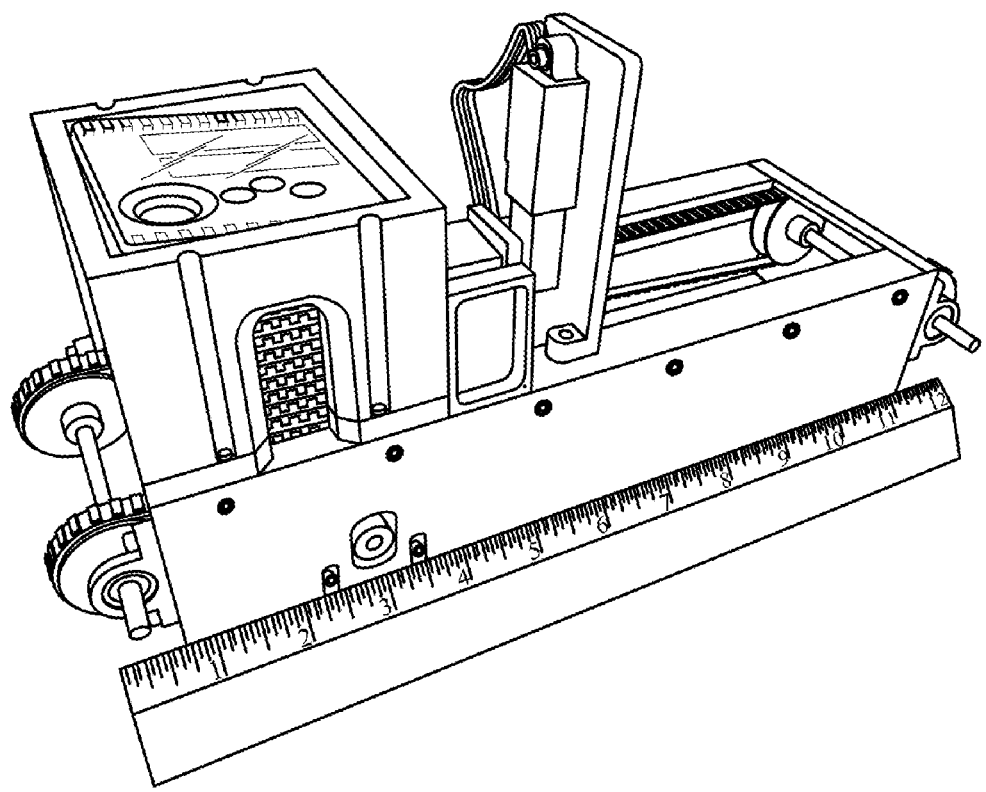
FIG. 8 shows an exemplary prototype, approximate size 14×6×8 inches.

The present invention relates to an exemplary system configured to conduct autonomous surveillance of a pathogen (e.g., present in an organism, such as a mosquito). The system can have any useful component, e.g., as described in FIG. 7 and herein. In one instance, the system includes a cartridge (e.g., an assay chip carrier having a plurality of cartridges), a port configured to receive an organism and obtain a test sample from the organism (e.g., mosquito portal), a heating module (e.g., a thermal block module), a detection module (e.g., a fluorescence detector module and detector electronics), a processing module (e.g., electronics), a power source (e.g., a battery pack), and a motor module (e.g., drive motor and belt tensioner). Optionally, the system can include a filling module configured to load agent(s) into the cartridge (e.g., by way of pump actuators). The system can be optionally provided in a single housing or enclosure (FIG. 8).

Example 4: Diagnostics with RT-LAMP

Figure 9:
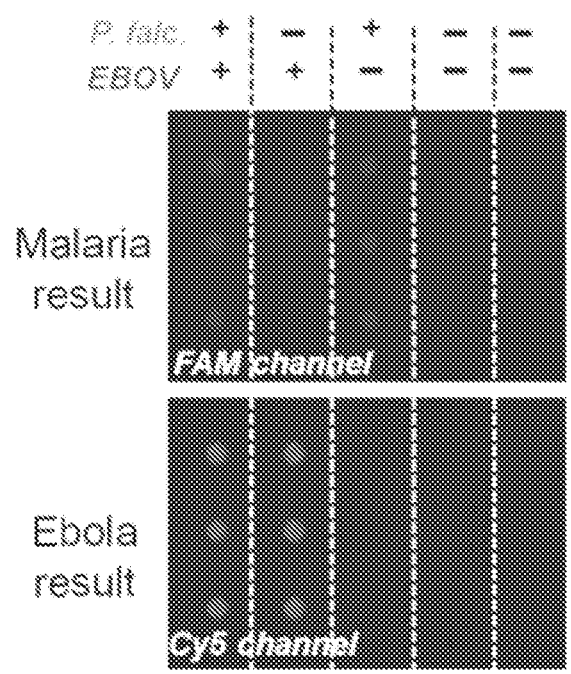
FIG. 9 shows single-tube multiplexed detection of Ebola and *Plasmodium*.

The cartridge can be configured to conduct any useful assay. In one non-limiting embodiment, the assay is configured for multiplexed detection by way of nucleic acid amplification (FIG. 9).

Example 5: Stabilized Agents

Figure 10:
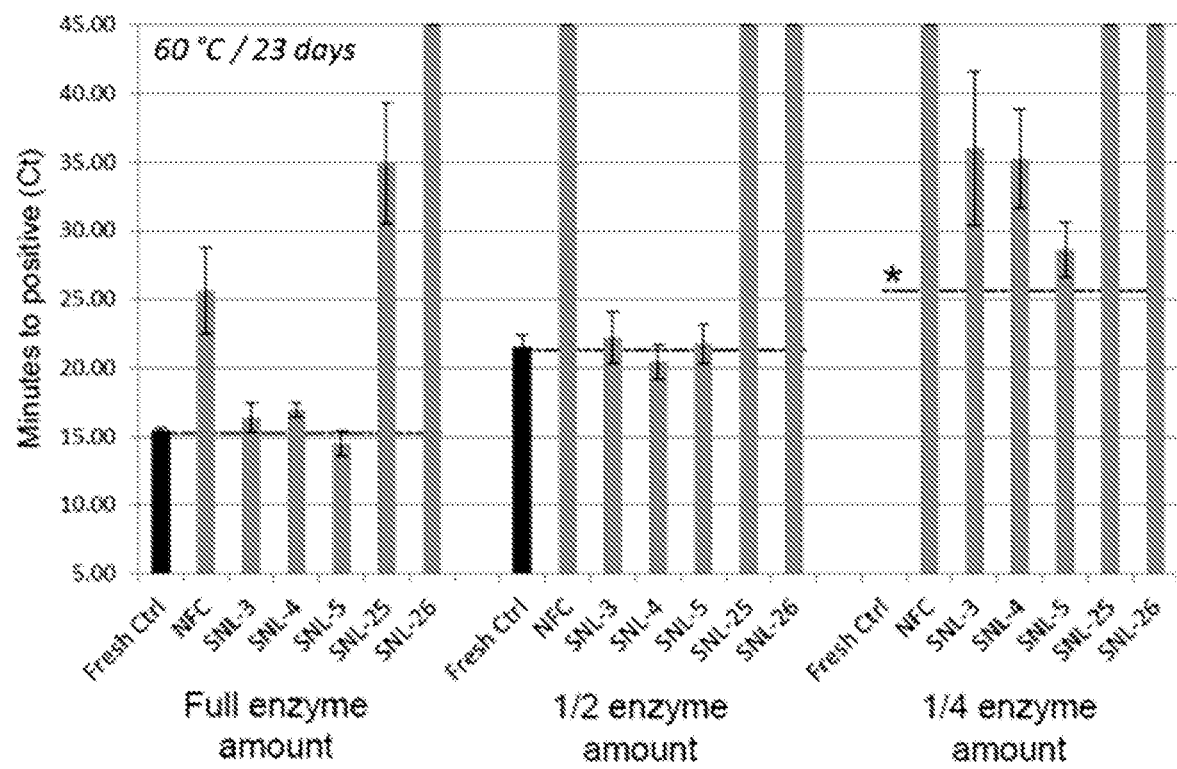
FIG. 10 shows results from formulated RT-LAMP assays for long-term stability in dry form in storage on as assay chip, which can be rehydrated with bait fluid to perform an assay. Minimal loss in activity was observed, even after >3 weeks at 60° C., even with reduced enzyme.

The cartridge can include one or more stabilized agents (e.g., an assay agent including one or more stabilizing agents, such as any described herein). FIG. 10 provides long-term stability data for RT-LAMP agent stored on-chip with stabilizing agents.

Example 6. Exemplary Mosquito Bait

The system and cartridges can include the use of a bait to attract organisms for sample collection. In one instance, the cartridge includes a sample port having a bait to attract mosquitoes, which in turn results in the collection and analysis of mosquito saliva for further analysis.

The sample port can include (e.g., be in proximity to) any useful bait. In one non-limiting instance, the bait includes a solid bait (e.g., hard candy, spun floss, a pellet, such as a porous pellet, etc.). In particular, we developed various protocols to form spun floss from liquid flavoring ingredients. The addition of an excipient (e.g., poly(ethylene glycol) or PEG) provided enhanced material properties (e.g., structural resistance to moisture, etc.). Exemplary recipes and compositions for the bait can include of from about 1 wt % to 70 wt % PEG (e.g., having a molecular weight of from about 1 kDa to about 100 kDa, such as of from about 5 wt % to 50 wt % PEG), 0.5 wt % to 95 wt % sugar (e.g., granulated sugar), 0 wt % to 10 wt % honey, as well as optional fragrance(s), coloring(s), dye(s), etc. The recipe can be processed in any useful manner (e.g., as described herein).

Exemplary processes to form a bait include the following:

Process A
1. Preheat machine (e.g., a candy cotton candy maker)
2. Add 10 g total of a premixed recipe for the bait composition (e.g., including ingredients such as PEG, sugar, honey, food coloring, etc.) into the cotton candy machine
3. Turn on the machine and collect the candy onto a plastic stick, as per instructions Process B
1. Melt the ingredients of the recipe for the bait composition (e.g., any recipe herein) in a disposable aluminum dish on a hot plate until just melted
2. Mix with a wooden stick until even
3. Cool the mixture on the counter, which then forms a "hard candy"
4. Break off 10 g of hard candy, and add to the cool (or preheated) machine
5. Collect as instructed Process C
1. Add water to ingredients of the recipe for the bait composition, and stir over heat to dissolve
2. Stop stirring; track the temperature until about 155° C.
3. Remove from heat; cool rapidly by dipping the melted candy mixture into liquid nitrogen
4. Add 10 g of resultant hard candy to machine and use per instructions Process D
1. Same as Process C, step 1
2. Same as Process C, step 2
3. Remove from heat and place on steel block to cool slowly.
4. Same as Process C, step 4

Process E
1. Same as Process B, step 1
2. Same as Process B, step 2
3. Remove from heat; cool rapidly by dipping the melted candy mixture into liquid nitrogen
4. Same as Process B, step 4
5. Same as Process B, step 5

The recipes and composition of the bait (e.g., cotton candy) can include, e.g., the following variations:
- 9.5 g white granulated sugar, 0.5 g PEG (e.g., 20 kDa MW), 2 drops of food coloring
- 7.5 g sugar, 2.5 g PEG, 2 drops of food coloring
- 5 g sugar, 5 g PEG, 2 drops of food coloring
- 9 g sugar, 0.5 g PEG, 0.5 g honey
- 17 g sugar, 2 g PEG, 1 g honey, 0.05 g food coloring
- 18 g sugar, 2 g PEG, 0.05 g food coloring The presence of assay reagents (e.g., RT-LAMP reagents) within the bait may be repellent to mosquitos. Thus, in one non-limiting embodiment, the bait does not include the reaction buffer. In another embodiment, the bait includes dried components, in which reagents and enzymes for the assay are provided as dried agents separate from the bait.

Figure 11:
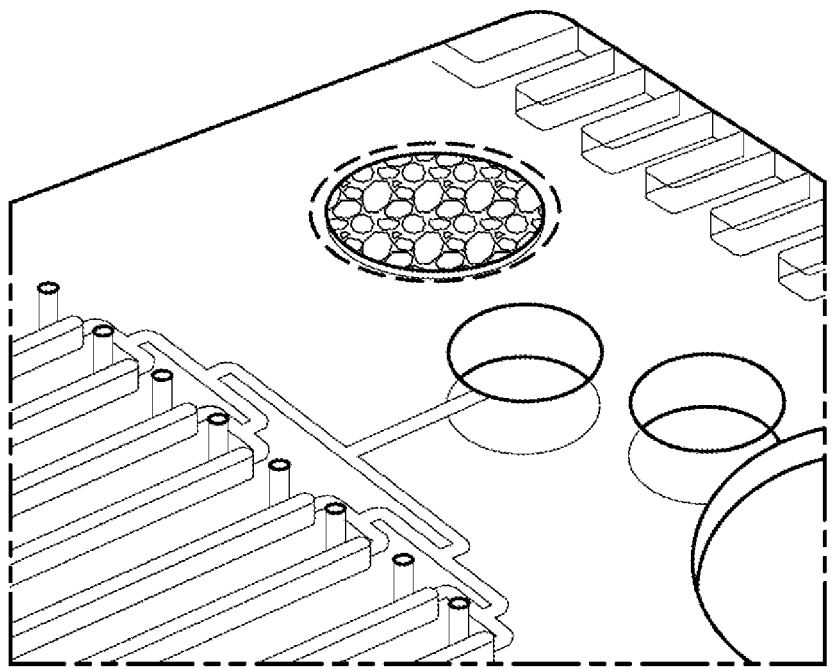
FIG. 11 shows a corner of an exemplary assay cartridge including a dyed, polymer-modified bait (indicated by dashed lines).

One strategy for a solid bait that we tested was a "cotton candy" or spun sugar bait (FIG. 11). The cotton candy could be pressed into the feeding well, over and on top of a dried enzyme pellet and a ball bearing for magnetic mixing. We anticipated this would allow a large surface area for mosquitoes to feed, as well as dissolve instantly upon adding a drop of rehydration buffer. Plain cotton candy made from pure sucrose turned out to be unstable upon storage for more than a few days, and we subsequently devised a way to modify the cotton candy by melting a polymer (PEG) with the sugar prior to spinning, to stabilize it against shriveling in ambient humidity. In relatively small trials observing mosquito preferences for cotton candy baits with various scented attractants added on top, it was determined that both honey and plumeria were attractive to mosquitoes, over and above phenylacetaldehyde (which had been used previously in the field, and is one of the scented components in honey). Based on this experiment (Table 1), we determined that both honey and plumeria could be used as attractants for sugar-feeding *Culex tarsalis* mosquitoes.

TABLE 1

Observations of number of mosquitoes feeding upon scented, spun baits

| | Number of mosquitos observed feeding each scent | | | |
|---|---|---|---|---|
| | Plumeria | Honey | Phenylacetaldehyde | Control |
| Day 0 | 0 | 7 | 0 | 0 |
| Day 1 | 6 | 3 | 5 | 2 |
| Day 2 | 7 | 4 | 1 | 2 |
| Day 3 | 7 | 1 | 4 | 2 |
| Day 4 | 5 | 6 | 3 | 2 |
| Sum | 25 | 21 | 13 | 8 |

A second feeding experiment was performed using a liquid sugar bait, which include a tube of sugar solution with a cotton ball, either with or without honey smeared on the cotton, and presented to the colony for feeding. The mosquitoes consumed twice as much liquid from the bait flavored with honey. This further confirms that the scent of honey is attractive to *Culex tarsalis* mosquitoes, at least in a laboratory setting.

Example 7. Smart Trap Having a Rotary Design

Rather than the "stack" of chips driven by a conveyor belt, the cartridges (or chips) can be arranged in a carousel format, with a stepper motor capable of rotating the carousel a fixed angle (e.g., 20°) each day. Furthermore, a stepper motor with absolute position encoding could enable precise placement of chips. The chips could still be fabricated as individual daily-use consumables, perhaps in a pie-shaped format, and used to populate a circular frame.

Furthermore, this Smart Trap with carousel could have an overall cylindrical format. If sized properly, this format could be housed inside of a field trap (e.g., a BG-Sentinel trap, from BioGents AG, Regensburg, Germany). Such a trap can capture and retain organisms (e.g., mosquitoes) within a larger field trap, into which a Smart Trap can be located, thereby increasing the probability that a trapped organism (within the field trap) would enter the portal of a Smart Trap system. In addition, retention of organisms in the field trap would provide an ability to verify presence of these organisms, as well as provide estimates of abundance and species of each organism at least for the overall period of trap deployment (if not for any specific day). A simple optical detector could further allow measurement of number of insects collected per night (if not the species identity).

Figure 12A:
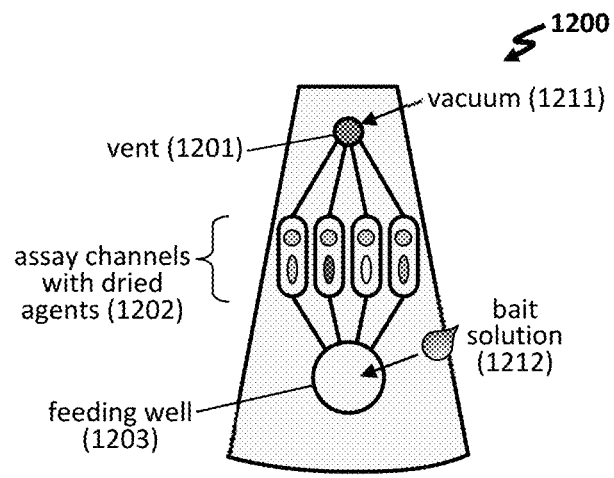
FIG. 12A-12B shows (A) an exemplary cartridge 1200 and (B) a carousel 1250 including a plurality of cartridges.
Figure 12B:
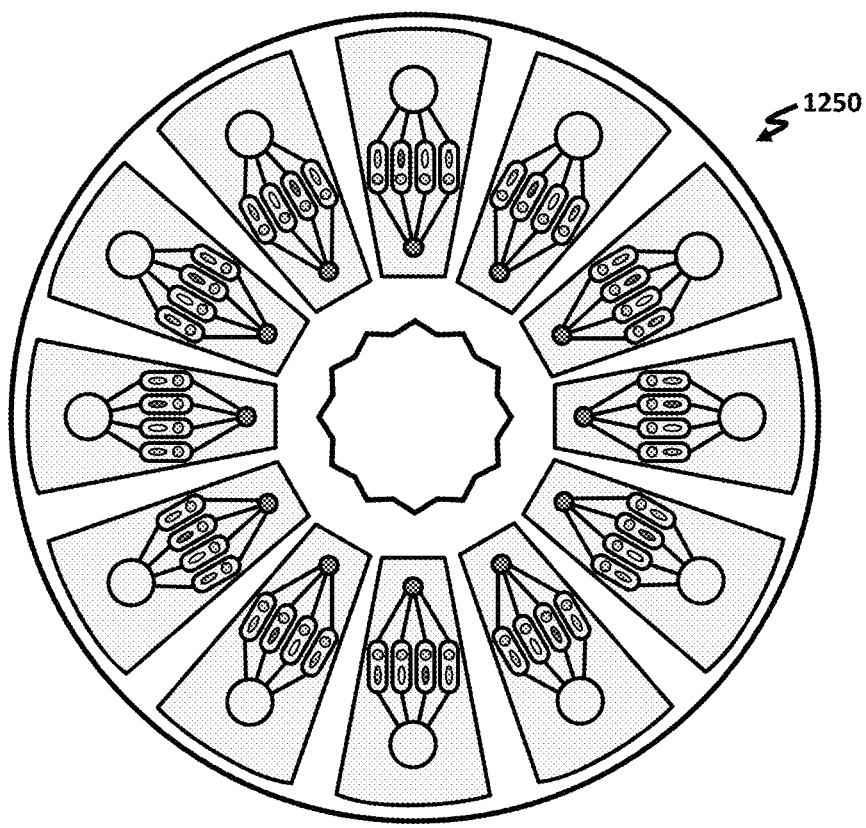

FIG. 12A provides for a schematic for an exemplary disposable assay cartridge 1200 having a vent 1201 (in which vacuum 1211 can be optionally applied to load agents on the chip), one or more assay channels including the one or more agents to conduct the assay 1202, and a feeding well 1203 (into which a bait solution 1212 can be injected or stored). FIG. 12B provides a plurality of cartridges designed to fit into a circular carousel tray 1250 to operate with a rotating mechanism. Note a carousel with 12 positions is shown for simplicity of drawing, but configurations with, e.g., 30 daily cartridges are possible.

Figure 13:
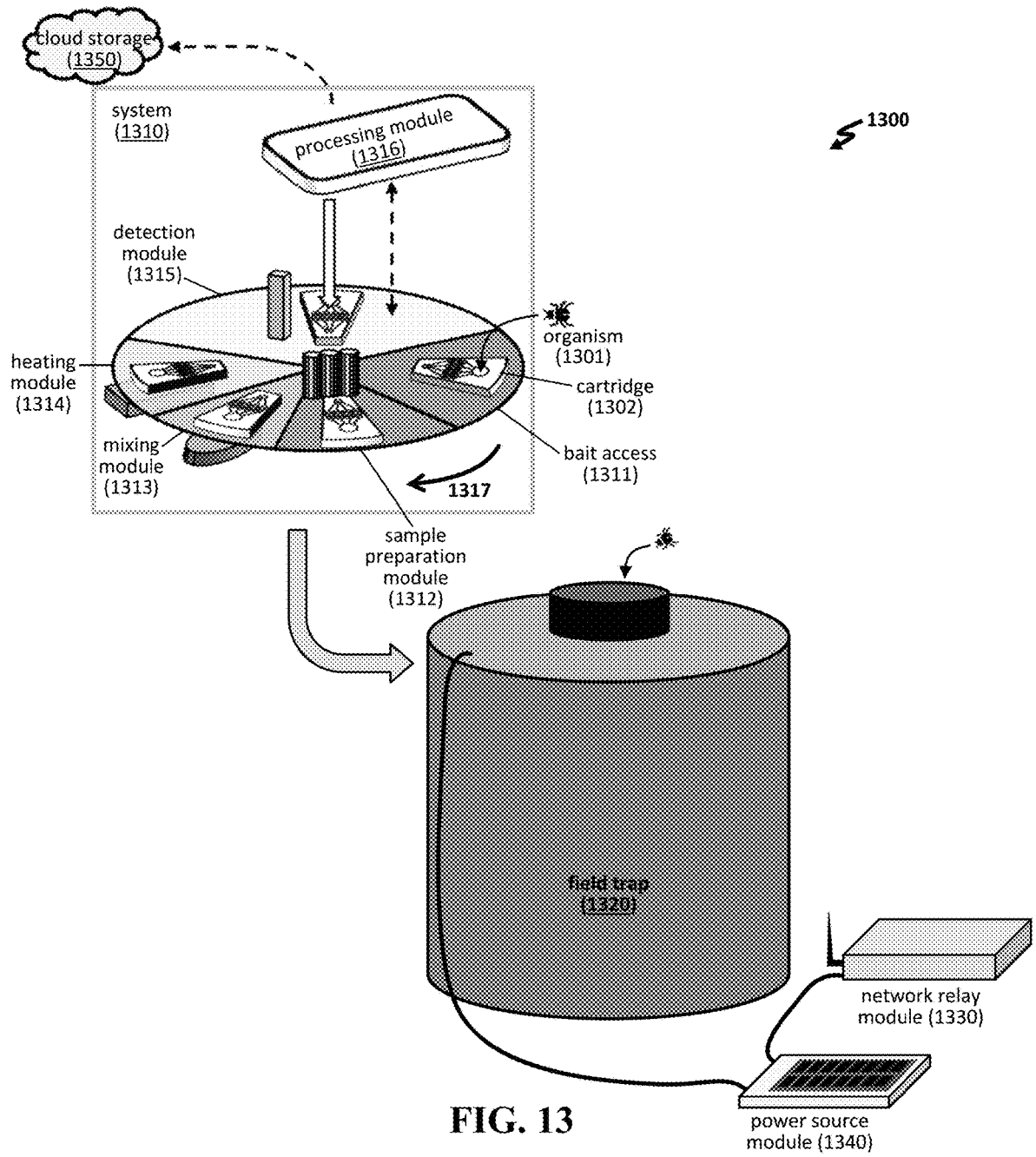
FIG. 13 shows an assembly 1300 including an exemplary Smart Trap system 1310 within a field trap 1320.

FIG. 13 provides an exemplary assembly 1300 including a Smart Trap system 1310 disposed within a field trap 1320, connected to a network relay module 1330 and an external power source module 1340 (e.g., a solar power battery). In this exemplary embodiment, the processing module 1316 (e.g., a smart phone or another mobile computing device) can provide an optional communication link to a cloud storage system 1350. Alternatively, obtained data can be provided from the processing module to the network relay module, which can then transmit the data to cloud storage system.

As can be seen, the Smart Trap system 1310 can be designed in a rotary format, in which a cartridge 1302 is mounted on a carousel format. The individual chip in use can be rotated 1317 to the necessary positions and stations, e.g., a bait access region 1311 having a port for access by an organism 1301, a positioning module for feeding, a sugar bait loading module, a sample preparation module 1312 having reagent reservoirs and/or pumps to load reagents into the cartridge, a mixing module 1313 having a mixer to combine the test sample with an agent to conduct the assay, a heating module 1314 having a heater to provide assay conditions (e.g., for a RT-LAMP assay), and/or a detection module 1315 including an LED array to provide an excitation wavelength, in which emission can be detected and/or transmitted by the processing module 1316), using a motor module (e.g., a stepper motor with absolute position encoding).

In one non-limiting embodiment, the cartridge includes a feeding well and a feeding well configured to obtain the test sample from the organism; and one or more assay channels including the one or more agents to conduct the assay. The system can include a sample preparation module, which can include a fluid dispensing system configured to dispense a liquid bait within the feeding well of the cartridge. The fluid dispensing system can be further configured to dispense a buffer into the assay channel, thereby hydrating the assay agents. Filling of the assay channel (with the buffer) can be facilitated in any useful manner, e.g., use of a hydrophobic vent at the end of the channels allowing air to pass through but not fluid, in which vacuum or suction can be applied to the vent to facilitate fluid flow; use of a linear actuator to press-seal a gasket (e.g., a silicone gasket) against the inlet and outlet vents.

A processing module 1316 (e.g., a smartphone) integral to the system controls these operations and performs final interrogation of the assay. The remaining chips on the carousel are not shown but would essentially remain "inert" (unaffected by the operations occurring to the active chip). The entire assembly is housed within a field trap (e.g., a BG-Sentinel trap, which can be fitted with host-seeking attractants and/or $CO_2$ from a tank, if desired, in which the fan for the BG Sentinel trap can be powered continuously or semi-continuously using power from a solar-charged battery or solar power bank). An external power source module 1340 can also power additional external electronics (e.g., a network relay module 1330, such as an XBEE radio module for private wireless networking as in the current system, should the trap be positioned outside the range for the integral smartphone to transmit data to the cloud).

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A system comprising:
a port that receives a mosquito or tick;
a circular carousel tray;
cartridges included in the circular carousel tray, where the cartridges are arranged symmetrically around a center of the circular tray, and further wherein the cartridges comprise a cartridge;
a stepper motor that rotates the circular carousel tray, wherein the cartridges in the circular carousel tray progress through different stations of the system as the circular carousel tray is rotated by the stepper motor, where the stations include:
a bait loading station that loads bait into a feeding well of the cartridge, the bait attracts the mosquito or tick to the bait;
an access station where the bait loaded onto the cartridge is accessed by the mosquito or tick by way of the port;
a sample preparation station that causes an agent retained in an assay channel of the cartridge to enter the feeding well with the bait to form a sample, wherein the sample preparation station includes a fluid dispensing system that dispenses a fluid buffer into the feeding well, wherein the cartridge includes a hydrophobic vent at an end of the assay channel that allows air to pass through but prevents the fluid buffer from passing through, and further wherein a vacuum is applied to the vent to facilitate flow of the fluid buffer from the feeding well into the assay channel;

a mixing station that includes a mixer that mixes the sample such that an assay for detecting a target nucleic acid is conductible;

a heating station that has a heater that provides assay conditions by heating the sample, and a detection station that includes a light source that provides light having an excitation wavelength towards the mixed and heated sample, wherein the cartridge conducts the assay, wherein the target nucleic acid indicates presence of a pathogenic nucleic acid in the sample; and a processing module configured to generate a signal to the heating station, the detection station, and/or the stepper motor and further configured to receive a detectable signal from the detection station, wherein the detectable signal is based upon the light having the excitation wavelength, and further wherein the detectable signal indicates whether or not the tick or mosquito deposited the pathogenic nucleic acid on the bait.

2. The system of claim 1, wherein the pathogenic nucleic acid is obtained from Zika virus, Zaire ebolavirus (EBOV), West Nile Virus (WNV), Chikungunya Virus (CHIKV), Western Equine Encephalitis Virus (WEEV), St. Louis Encephalitis Virus (SLEV), Dengue Virus (DENY), Marburg virus (MARV), Sudan ebolavirus (SUDV), Bundibugyo virus (BDBV), Yellow Fever Virus (YFV), Japanese Encephalitis Virus (JEV), Hepatitis C virus (HCV), Eastern Equine Encephalitis Virus (EEEV) Venezuelan Equine Encephalitis Virus (VEEV), Sindbis virus (SINV), Ross River virus (RRV), influenza virus, hantavirus, Rift Valley Fever virus, Crimean-Congo hemorrhagic fever virus, Lassa Fever virus, or norovirus.

3. The system of claim 1, wherein the cartridge comprises one or more unidirectional check valves.

4. The system of claim 1, wherein the agent in the assay channel is a dried reagent.

5. The system of claim 1, wherein the cartridge further comprises:

a fluid reservoir comprising the fluid buffer and a membrane configured to dispense the fluid buffer upon actuation.

6. The system of claim 1, wherein the bait is a dehydrated bait or a solid bait, the system further comprising:

a fluid reservoir comprising the fluid buffer and a membrane configured to dispense the fluid buffer upon actuation;

a first unidirectional check valve configured to deliver the fluid buffer to the feeding well; and a second unidirectional check valve configured to deliver the sample from the feeding well to the assay channel.

7. The system of claim 6, further comprising:

an actuator that actuates the membrane of the cartridge.

8. The system of claim 6, wherein the feeding well further comprises a metal ball bearing.

9. The system of claim 8, further comprising:

a spinning magnet that rotates the metal ball bearing within the feeding well.

10. The system of claim 1, wherein the cartridge conducts a multiplexed assay.

11. The system of claim 1, wherein the assay comprises:

a first primer comprising a first nucleic acid sequence having sufficient complementarity to bind to a site in the pathogenic nucleic acid; and a quench probe comprising a second nucleic acid sequence having sufficient complementarity to bind to a first portion of the first primer and further comprising a quencher label operably linked to the second nucleic acid sequence, wherein a melting temperature $T_m$ of the quench probe is less than about 65° C.

12. The system of claim 1, further comprising:

a network relay module that relays an electronic signal from the processing module, wherein the electronic signal is based upon the detectable signal.

13. The system of claim 1 being comprised by an assembly, the assembly comprising:
- a field trap that houses the system and traps a plurality of mosquitos;
- a network relay module that relays an electronic signal from the processing module; and
- an external power source module that provides power to the system, the field trap, and/or the network relay module.

14. The system of claim 1, wherein the agent comprises a first primer, a first quench probe, a first signal probe, a second primer, a second quench probe, and/or a second signal probe.

15. The system of claim 14, wherein the agent is a stabilizing agent.

16. The system of claim 1, wherein the bait included in the bait station is a spun sugar bait.

17. The system of claim 1, wherein the bait included in the bait station includes poly(ethylene glycol).

18. The system of claim 17, wherein the bait included in the bait station includes between 1% and 70% poly(ethylene glycol) by weight, between 0.5% and 95% of granulated sugar by weight, and honey.

19. The system of claim 1, wherein an order that the cartridge progresses through the stations as the stepper motor rotates the carousel is the bait loading station followed by the access station followed by the sample preparation station followed by the mixing station followed by the heating station followed by the detection station.

* * * * *